(12) United States Patent
Fertig et al.

(10) Patent No.: US 9,988,458 B2
(45) Date of Patent: Jun. 5, 2018

(54) ANTIBODIES AGAINST HUMAN CSF-1R AND USES THEREOF

(71) Applicant: HOFFMANN-LA ROCHE INC., Little Falls, NJ (US)

(72) Inventors: Georg Fertig, Penzberg (DE); Alexander Fidler, Penzberg (DE); Klaus Kaluza, Weilheim (DE); Marlene Thomas, Penzberg (DE); Carola Ries, Penzberg (DE); Stefan Seeber, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days. days.

(21) Appl. No.: 15/285,120

(22) Filed: Oct. 4, 2016

(65) Prior Publication Data

US 2017/0114139 A1    Apr. 27, 2017

Related U.S. Application Data

(62) Division of application No. 14/642,101, filed on Mar. 9, 2015, now Pat. No. 9,617,342, which is a division of application No. 13/582,964, filed as application No. PCT/EP2011/053214 on Mar. 3, 2011, now Pat. No. 9,169,323.

(30) Foreign Application Priority Data

Mar. 5, 2010    (EP) .................................... 10002268

(51) Int. Cl.
*C07K 16/28*    (2006.01)
*A61K 47/68*    (2017.01)

(52) U.S. Cl.
CPC ...... *C07K 16/2866* (2013.01); *A61K 47/6849* (2017.08); *C07K 16/28* (2013.01); *C07K 2317/14* (2013.01); *C07K 2317/21* (2013.01); *C07K 2317/24* (2013.01); *C07K 2317/34* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,202,238 A | 4/1993 | Fell, Jr. et al. |
| 5,204,244 A | 4/1993 | Fell et al. |
| 5,208,020 A | 5/1993 | Chari et al. |
| 5,416,064 A | 5/1995 | Chari et al. |
| 5,635,483 A | 6/1997 | Pettit et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,866,114 A | 2/1999 | Pandit et al. |
| 5,877,296 A | 3/1999 | Hamann et al. |
| 6,184,354 B1 | 2/2001 | Koths et al. |
| 6,630,579 B2 | 10/2003 | Chari et al. |
| 7,108,852 B2 | 9/2006 | Devalaraja et al. |
| 7,498,298 B2 | 3/2009 | Doronina et al. |
| 8,182,813 B2 | 5/2012 | Brasel et al. |
| 8,470,977 B2 | 6/2013 | Haegel et al. |
| 8,604,170 B2 | 12/2013 | Haegel et al. |
| 8,999,327 B2 | 4/2015 | Dimoudis et al. |
| 9,169,323 B2 | 10/2015 | Fertig et al. |
| 9,192,667 B2 | 11/2015 | Hoves et al. |
| 9,221,910 B2 | 12/2015 | Fertig et al. |
| 9,499,624 B2 | 11/2016 | Dimoudis et al. |
| 9,499,625 B2 | 11/2016 | Dimoudis et al. |
| 9,499,626 B2 | 11/2016 | Dimoudis et al. |
| 9,617,342 B2 | 4/2017 | Fertig et al. |
| 9,624,302 B2 | 4/2017 | Fertig et al. |
| 9,663,580 B2 | 5/2017 | Dimoudis et al. |
| 9,879,085 B2 | 1/2018 | Dimoudis et al. |
| 2002/0141994 A1 | 10/2002 | Devalaraja et al. |
| 2007/0280935 A1 | 12/2007 | Bohrmann et al. |
| 2009/0317403 A1 | 12/2009 | Aharinejad et al. |
| 2011/0081353 A1 | 4/2011 | Haegel et al. |
| 2011/0165156 A1 | 7/2011 | Dimoudis et al. |
| 2011/0178278 A1 | 7/2011 | Haegel et al. |
| 2011/0274683 A1 | 11/2011 | Wong et al. |
| 2012/0329997 A1 | 12/2012 | Fertig et al. |
| 2013/0005949 A1 | 1/2013 | Fertig et al. |
| 2013/0289250 A1 | 10/2013 | Haegel et al. |
| 2014/0057972 A1 | 2/2014 | Haegel et al. |
| 2014/0079706 A1 | 3/2014 | Cannarile et al. |
| 2014/0314771 A1 | 10/2014 | Hoves et al. |
| 2014/0336363 A1 | 11/2014 | Fertig et al. |
| 2015/0073129 A1 | 3/2015 | Herting et al. |
| 2015/0080556 A1 | 3/2015 | Fertig et al. |
| 2015/0158950 A1 | 6/2015 | Dimoudis et al. |
| 2015/0175696 A1 | 6/2015 | Fertig et al. |
| 2015/0274830 A1 | 10/2015 | Dimoudis et al. |
| 2015/0274831 A1 | 10/2015 | Dimoudis et al. |
| 2016/0053015 A1 | 2/2016 | Fertig et al. |
| 2016/0220669 A1 | 8/2016 | Hoves et al. |
| 2017/0015752 A1 | 1/2017 | Fertig et al. |
| 2017/0029517 A1 | 2/2017 | Dimoudis et al. |
| 2017/0051065 A1 | 2/2017 | Herting et al. |
| 2017/0247459 A1 | 8/2017 | Cannarile et al. |
| 2017/0275368 A1 | 9/2017 | Fertig et al. |

FOREIGN PATENT DOCUMENTS

| | | |
|---|---|---|
| EP | 0307434 B2 | 3/1989 |
| EP | 0668914 B1 | 8/1995 |

(Continued)

OTHER PUBLICATIONS

Abu-Duhier et al., "Mutational analysis of class III receptor tyrosine kinases (C-KIT, C-FMS, FL T3) in idiopathic myelofibrosis," Br J Haematol. 120(3):464-470 (2003).

(Continued)

*Primary Examiner* — Elly-Gerald Stoica
(74) *Attorney, Agent, or Firm* — Morrison & Foerster LLP

(57) ABSTRACT

The present invention relates to antibodies against human CSF-1R (CSF-1R antibody), methods for their production, pharmaceutical compositions containing said antibodies, and uses thereof.

14 Claims, 1 Drawing Sheet

(56) References Cited

FOREIGN PATENT DOCUMENTS

| | | |
|---|---|---|
| EP | 0425235 B1 | 9/1996 |
| EP | 2423228 A1 | 2/2012 |
| JP | H0967400 A | 3/1997 |
| JP | 2001-523956 A | 11/2001 |
| JP | 2006-519163 A | 8/2006 |
| JP | 2008-013566 A | 1/2008 |
| JP | 2010-536378 A | 12/2010 |
| JP | 2011-512851 A | 4/2011 |
| JP | 2013-513367 A | 4/2013 |
| JP | 2016-531150 A | 10/2016 |
| RU | 2008132150 A | 2/2010 |
| WO | WO-93/025687 A1 | 12/1993 |
| WO | WO-94/11026 A2 | 5/1994 |
| WO | WO-1998/43089 A1 | 10/1998 |
| WO | WO-98/52976 A1 | 11/1998 |
| WO | WO-99/017798 A1 | 4/1999 |
| WO | WO-01/30381 A2 | 5/2001 |
| WO | WO-2004/045532 A2 | 6/2004 |
| WO | WO-2005/046657 A2 | 5/2005 |
| WO | WO-2006/012451 A2 | 2/2006 |
| WO | WO-2006/096489 A2 | 9/2006 |
| WO | WO-2007/075326 A2 | 7/2007 |
| WO | WO-2007/081879 A2 | 7/2007 |
| WO | WO-2008/153926 A2 | 12/2008 |
| WO | WO-2008/153926 A3 | 12/2008 |
| WO | WO-2008/153926 A4 | 12/2008 |
| WO | WO-2009/026303 A1 | 2/2009 |
| WO | WO-2009/112245 A1 | 9/2009 |
| WO | WO-2009/120903 A2 | 10/2009 |
| WO | WO-2011/070024 A1 | 6/2011 |
| WO | WO-2011/107553 A1 | 9/2011 |
| WO | WO-2011/117329 A1 | 9/2011 |
| WO | WO-2011/123381 A1 | 10/2011 |
| WO | WO-2011/131407 A1 | 10/2011 |
| WO | WO-2011/140249 A2 | 11/2011 |
| WO | WO-2012/110360 A1 | 8/2012 |
| WO | WO-2013/087699 A1 | 6/2013 |
| WO | WO-2013/132044 A1 | 9/2013 |
| WO | WO-2014/173814 A1 | 10/2014 |
| WO | WO-2015/036511 A1 | 3/2015 |

OTHER PUBLICATIONS

Affymetrix Ebioscience. (2000-2014). "Anti-Mouse CD115 (c-fms) Purified," located at <http://www.ebioscience.com/mouse-cd115-antibody-purified-afs98.htm, last visited on Mar. 26, 2015, one page.
Aharinejad et al., "Colony-stimulating factor-1 blockade by antisense oligonucleotides and small interfering RNAs suppresses growth of human mammary tumor xenografts in mice," CancerRes. 64(15):5378-5384(2004).
Anonymous (1988). "MCSF Receptor antibody (ab 10676)" 38 pages.
Ashmun et al., "Monoclonal antibodies to the human CSF-1 receptor (c-fms proto-oncogene product) detect epitopes on normal mononuclear phagocytes and on human myeloid leukemic blast cells" Blood 73(3):827-37 (Feb. 15, 1989).
Baker et al., "Expression of the colony-stimulating factor 1 receptor in B lymphocytes," Oncogene. 8(2):371-378 (1993).
Balkwill et al., "Smoldering and polarized inflammation in the initiation and promotion of malignant disease," Cancer Cell. 7(3):211-217 (2005).
Balkwill, "TNF-alpha in promotion and progression of cancer," Cancer Metastasis Rev. 25(3):409-416 (2006).
Barnes et al., "Advances in animal cell recombinant protein production: GS-NSO expression system," Cytotechnology. 32(2): 109-123 (2000).
Barnes et al., "Characterization of the stability of recombinant protein production in the GS-NSO expression system," Biotechnol Bioeng. 73(4):261-270 (2001).
Beiboer et al., "Guided selection of a pan carcinoma specific antibody reveals similar binding characteristics yet structural divergence between the original murine antibody and its human equivalent," J Mol Biol. 296(3):833-849 (2000).
Bingle et al., The role of tumour-associated macrophages in tumour progression: implications for new anticancer therapies, J Pathol. 196(3):254-265 (2002).
Boackle et al., "An IgG primary sequence exposure theory for complement activation using synthetic peptides," Nature. 282(5740):742-743 (1979).
Boerner et al., "Production of antigen-specific human monoclonal antibodies from in vitro-primed human splenocytes," J Immunol. 147(1):86-95 (1991).
Bonham et al., "Antagonistic antibodies to c-fms block c-fms-mediated activities reduce tumor-associated macrophages and decrease tumor growth in preclinical models," In Proc Am Assoc Cancer Res 50:503. Abstract #2077 (2009).
Bourette et al., "Early events in M-CSF receptor signaling," Growth Factors. 17(3): 155-166 (2000).
Bruggemann et al., "Designer mice: the production of human antibody repertoires in transgenic animals," Year Immunol. 7:33-40 (1993).
Brunhouse et al., "Isotypes of IgG: comparison of the primary structures of three pairs of isotypes which differ in their ability to activate complement," Mol Immunol. 16(11):907-917 (1979).
Burmester et al., "Mavrilimumab, a human monoclonal antibody targeting GM-CSF receptor[alpha], in subjects with rheumatoid arthritis: a randomised, double-blind, placebo-controlled, phase 1, first-in-human study," Ann Rheum Dis. 70(9):1542-9 (2011).
Burton et al., "The C1q receptor site on immunoglobulin G," Nature. 288:338-344 (1980).
Campbell et al., "The colony-stimulating factors and collagen-induced arthritis: exacerbation of disease by M-CSF and G-CSF and requirement for endogenous M-CSF," J Leukoc Biol. 68(1):144-150 (2000).
Carter et al., "Humanization of an anti-p185HER2 antibody for human cancer therapy," Proc Natl Acad Sci US A. 89(10):4285-4289 (1992).
Casset et al., "A peptide mimetic of an anti-CD4 monoclonal antibody by rational design," Biochem Biophys Res Commun. 307:198-205 (2003).
Cenci et al., "M-CSF neutralization and Egr-1 deficiency prevent ovariectomy-induced bone loss," J Clin Invest. 105(9):1279-1287 (2000).
Chari et al., "Immunoconjugates containing novel maytansinoids: promising anticancer drugs," Cancer Res. 52(1):127-131 (1992).
Chase et al., "Imatinib sensitivity as a consequence of a CSF1 R-Y571 D mutation and CSF1/CSF1 R signaling abnormalities in the cell line GDM1," Leukemia. 23(2):358-364 (2009).
Choueiri et al., "The central role of osteoblasts in the metastasis of prostate cancer," Cancer Metastasis Rev. 25(4):601-609 (2006).
Cole et al., "The EBV-hybridoma technique and its application to human lung cancer," Monoclonal Antibodies and Cancer Therapy. Alan R. Liss, Inc. 77-96 (1985).
Coussens et al., "Structural alteration of viral homologue of receptor proto-oncogene fms at carboxyl terminus," Nature. 320(6059):277-280 (1986).
da Costa et al., "Presence of osteoclast-like multinucleated giant cells in the bone and nonostotic lesions of Langerhans cell histiocytosis," J Exp Med. 201(5):687-693 (2005).
Dai et al., "Targeted disruption of the mouse colony-stimulating factor 1 receptor gene results in osteopetrosis, mononuclear phagocyte deficiency, increased primitive progenitor cell frequencies, and reproductive defects," Blood. 99(1):111-120 (2002).
Daroszewska et al., "Mechanisms of disease: genetics of Paget's disease of bone and related disorders," Nat Clin Pract Rheumatol. 2(5):270-277 (2006).
Davies et al., "Affinity improvement of single antibody VH domains: residues in all three hypervariable regions affect antigen binding," Immunotechnology. 2(3):169-179 (1996).
DeNardo et al., "Leukocyte complexity predicts breast cancer survival an dfunctionally regulates response to chemotherapy," Cancer Research 1(1) pp. 1-15, (Apr. 2011).

(56) References Cited

OTHER PUBLICATIONS

Dewar et al., "Macrophage colony-stimulating factor receptor c-fms is a novel target of imatinib," Blood, 105(8):3127-32, (2005).
Drees et al., "Mechanisms of disease: Molecular insights into aseptic loosening of orthopedic implants," Nat Clin Pract Rheumatol. 3(3):165-171 (2007).
Dubowchik et al., "Doxorubicin immunoconjugates containing bivalent, lysosomally-cleavable dipeptide linkages," Bioorg Med Chern Lett. 12(11): 1529-1532 (2002).
Durocher et al., "High-level and high-throughput recombinant protein production by transient transfection of suspension-growing human 293-EBNA1 cells," Nucleic Acids Res. 30(2):E9 (2002).
English Translation of Notification of Reasons for Rejection for Japanese Patent Application No. 2012-542522, dated Feb. 25, 2014 (3 pages).
European Search Report for Application No. EP 09007224.0 pp. 1-9 dated Nov. 24, 2009.
European Search Report for Application No. EP 09015310 pp. 1-8 dated Sep. 9, 2010.
Extended Search Report for European Patent Application No. EP 12158519.4, dated Aug. 2, 2012 (8 pages).
Feldstein et al., "Practice patterns in patients at risk for glucocorticoid-induced osteoporosis," Osteoporos Int. 16(12):2168-2174 (2005).
Flatman et al., "Process analytics for purification of monoclonal antibodies," J Chromatogr B Analyt Techno! Biomed Life Sci. 848{1):79-87 (2007).
Flick et al., "Recognition of activated CSF-1 receptor in breast carcinomas by a tyrosine 723 phosphospecific antibody," Oncogene 14:253-2561, (1997).
Geisse et al., "Eukaryotic expression systems: a comparison," Protein Expr Purif. 8(3):271-282 (1996).
Guzman-Clark et al., "Barriers in the management of glucocorticoid-induced osteoporosis," Arthritis Rheum. 57(1)140-146 (2007).
Hamilton, "Colony-stimulating factors in inflammation and auto-immunity," Nat Rev Immunol.8 (7):533-544 (2008).
Hao et al., "Expression of macrophage colony-stimulating factor and its receptor in microglia activation is linked to teratogen-induced neuronal damage," Neuroscience. 112(4):889-900 (2002).
Haran-Gehera et al., "Increased Circulating Colony-Stimulating Factor-1 (CSF-1) in SJL/J mice with radiation-induced acute myeloid leukemia (AML) is associated with autocrine regulation of AML cells by CSF-1," The American Society of Hematology 89(7):2537-2545, (Apr. 1, 1997).
Hayashi et al., "Osteoclast precursors in bone marrow and peritoneal cavity," J. Cell Physiol. 170(3):241-7, (Mar. 1997).
Hezareh et al., "Effector function activities of a panel of mutants of a broadly neutralizing antibody against human immunodeficiency virus type 1," J Viral. 75(24):12161-12168 (2001).
Hinman et al., "Preparation and characterization of monoclonal antibody conjugates of the calicheamicins: a novel and potent family of antitumor antibiotics," Cancer Res. 53(14):33363342 (1993).
Holt, L. et al., "Domain antibodies: proteins for therapy" Trends in Biotechnology. 21(11):484-490 (Nov. 1, 2003).
Hoogenboom et al., "By-passing immunisation. Human antibodies from synthetic repertoires of germline VH gene segments rearranged in vitro," J Mol Biol. 227(2):381-388 (1992).
Hume et al. (2012). "Therapeutic applications of macrophage colony-stimulating factor-1 (CSF-1) and antagonists of CSF-1 receptor (CSF-1R) signaling," Blood. Feb. 23, 2012;119(8):1810-20 (originally published online on Dec. 20, 2011).
Huston et al., "Protein engineering of single-chain Fv analogs and fusion proteins," Methods Enzymol. 203:46-88 (1991).
Ide et al., "Expression of colony-stimulating factor 1 receptor during prostrate development and prostate cancer progression," Proc. Natl. Acad. Sci. U.S.A. 99:14404-14409, (Oct. 29, 2002, e-pub. Oct. 15, 2002).

Idusogie et al., "Mapping of the C1 q binding site on rituxan, a chimeric antibody with a human IgG1 Fe," J Immunol. 164(8):4178-4184 (2000).
Ikonomidis et al., "Increased circulating C-reactive protein and macrophage-colony stimulating factor are complementary predictors of long-term outcome in patients with chronic coronary artery disease," Eur Heart J. 26(16):1618-1624 (2005).
Inaba et al., "Expression of M-CSF receptor encoded by c-fms on smooth muscle cells derived from arteriosclerotic lesion," J Biol Chern. 267(8):5693-5699 (1992).
International Search Report for International Patent Application No. PCT/EP2011/053214, dated Apr. 28, 2011 (6 pages).
International Search Report for International Patent Application No. PCT/EP2013/054676, dated May 7, 2013 (7 pages).
International Search Report for International Patent Application No. PCT/EP2012/075241, dated Feb. 22, 2013 (7 pages).
International Search Report for PCT Application No. PCT/EP2011/053213, dated on Sep. 1, 2011, filed on Mar. 3, 2011, 6 pages.
International Search Report for PCT Application No. PCT/EP2014/057909, dated Sep. 1, 2014, filed on Apr. 17, 2014, 6 pages.
International Search Report dated Nov. 18, 2014, for PCT Patent Application No. PCT/EP2014/069451, filed on Sep. 11, 2014, seven pages.
Jakobovits et al., "Analysis of homozygous mutant chimeric mice: deletion of the immunoglobulin heavy-chain joining region blocks B-cell development and antibody production," Proc Natl Acad Sci US A. 90(6):2551-2555 (1993).
Jakobovits et al., "Germ-line transmission and expression of a human-derived yeast artificial chromosome," Nature. 362(6417):255-258 (1993).
Jeffrey et al., "Dipeptide-based highly potent doxorubicin antibody conjugates," Bioorg Med Chern Lett. 16(2):358-362 (2006).
Johnson et al., "Kabat database and its applications: 30 years after the first variability plot," Nucleic Acids Res. 28(1):214-218 (2000).
Jose et al., "Blockade of macrophage colony-stimulating factor reduces macrophage proliferation and accumulation in renal allograft rejection," American Journal of Transplantation 3:394-300, (2003).
Kabat et al., "Tabulation and analysis of amino acid and nucleic acid sequences of precursors, v-regions, c-regions, j-chain, beta2-microglobulins, major histocompatibility antigens, thy-1, complement, c-reactive protein, thymopoietin, post-gamma globulin, and alpha2macroglobulin," Sequences of Proteins of Immunological Interest. U.S. Department of Health and Human Services, 10L (1983).
Kacinski et al., "Ovarian adenocarcinomas express fms-complementary transcripts and fms antigen, often with coexpression of CSF-1," American Journal of Pathology 137(1):135-147, (Jul. 1990).
Kacinski, "CSF-1 and its receptor in breast carcinomas and neoplasms of the female reproductive tract," Mol Reprod Dev. 46(1):71-74 (1997).
Kaku et al., "Amyloid beta protein deposition and neuron loss in osteopetrotic (op/op) mice," Brain Res Protoc. 12(2):1 04-108 (2003).
Kaufman, "Overview of vector design for mammalian gene expression," Mol Biotechnol. 16(2):151-160(2000).
Kawakami et al., "Macophage-colony stimulating factor inhibits the growth of human ovarian cancer cells in vitro," European Journal of Cancer 36:1991-1997, (2000).
King et al., "Monoclonal antibody conjugates of doxorubicin prepared with branched peptide linkers: inhibition of aggregation by methoxytriethyleneglycol chains," J Med Chern. 45(19):4336-4343 (2002).
Kirma et al., "Elevated expression of the oncogene c-fms and its ligand, the macrophage colony-stimulating factor-1, in cervical cancer and the role of transforming growth factor-beta1 in inducing c-fms expression," Cancer Res. 67(5):1918-1926 (2007).
Kitaura et al., "M-CSF mediates TNF-induced inflammatory osteolysis," J Clin Invest. 115(12):3418-3427 (2005).
Kitaura, H. et al., "An anti-c-Fms antibody inhibits orthodontic tooth movement," Journal of Dental Research 87(4):396-400 (Apr. 1, 2008).

(56) References Cited

OTHER PUBLICATIONS

Kommoss et al., "Co-expression of M-CSF transcripts and protein, FMS (M-CSF receptor) transcripts and protein, and steroid receptor content in adenocarcinomas of the ovary," Journal of Pathology 174:111-119, (1994).
Kratz et al., "Prodrugs of anthracyclines in cancer chemotherapy," Curr Med Chern. 13(5):477-523 (2006).
Lee et al., "The Cbl protooncoprotein stimulates CSF-1 receptor multiubiquitination and endocytosis, and attenuates macrophage proliferation," EMBO J. 18(13):3616-3628 (1999).
Lee, A. et al., "Functional dissection of structural domains in the receptor for colony-stimulating Factor-1*" The Journal of Biological Chemistry 267(23):16472-16483 (Aug. 15, 1992).
Lenda et al., "Reduced macrophage recruitment, proliferation, and activation in colony-stimulating factor-1-deficient mice results in decreased tubular apoptosis during renal inflammation," J Immunol. 170(6):3254-3262 (2003).
Lester et al., "Current management of treatment-induced bone loss in women with breast cancer treated in the United Kingdom," Br J Cancer. 94(1):30-35 (2006).
Li et al., "Role of dimerization and modification of the CSF-1 receptor in its activation and internalization during the CSF-1 response," The EMBO Journal 10(2):277-288, (1991).
Lin et al., "Discovery of a cytokine and its receptor by functional screening of the extracellular proteome," Science 320:807-811, (May 9, 2008).
Lode et al., "Targeted therapy with a novel enediyene antibiotic calicheamicin theta(I)1 effectively suppresses growth and dissemination of liver metastases in a syngeneic model of murine neuroblastoma," Cancer Res. 58(14):2925-2928 (1998).
Lukas et al., "Inhibition of C1-mediated immune hemolysis by monomeric and dimeric peptides from the second constant domain of human immunoglobulin G," J Immunol. 127(6):2555-2560 (1981).
MacCallum et al., "Antibody-antigen interactions: contact analysis and binding site topography," J Mol Biol. 262:732-745 (1996).
MacDonald et al., "An antibody against the colony-stimulating factor 1 receptor depletes the resident subset of monocytes and tissue-and tumor-associated macrophages but does not inhibit inflammation," Blood. 116(19):3955-63 (2010).
Makrides, "Components of vectors for gene transfer and expression in mammalian cells," Protein Expr Purif. 17(2): 183-202 (1999).
Mancino et al., "Breast cancer increases osteoclastogenesis by secreting M-CSF and upregulating RANKL in stromal cells," Journal of Surgical Research 100:18-24, (2001, e-pub. Jul. 24, 2001).
Mantovani et al., "The chemokine system in diverse forms of macrophage activation and polarization," Trends Immunol. 25(12):677-686 (2004).
Marks et al., "By-passing immunization. Human antibodies from V-gene libraries displayed on phage," J Mol Biol. 222(3):581-597 (1991).
Martin et al., "Growth and angiogenesis of human breast cancer in a nude mouse tumour model is reduced by NK4, a HGF/SF antagonist," Carcinogenesis. 24(8):1317-1323 (2003).
Morgan et al., "The N-terminal end of the CH2 domain of chimeric human IgG1 anti-HLA-DR is necessary for C1q, Fe gamma Rl and Fe gamma Rill binding," Immunology. 86(2):319-324 (1995).
Morrison et al., "Chimeric human antibody molecules: mouse antigen-binding domains with human constant region domains," Proc Natl Acad Sci US A. 81(21):6851-6855 (1984).
Murayama, T. et al., "Intraperitoneal administration of ant-c-fms monoclonal antibody prevents initial events of atherogenesis but does not reduce the size of advanced lesions in apolipoprotein E-deficient mice," Circulation 99(13)1 740-1746 (Apr. 6, 1999).
Murphy et al., "Expression of macrophage colony-stimulating factor receptor is increased in the AbetaPP(V717F) transgenic mouse model of Alzheimer's disease," Am J Pathol. 157(3):895-904 (2000).
Murphy et al., "Macrophage colony-stimulating factor augments beta-amyloid-induced interleukin-1, interleukin-6, and nitric oxide production by microglial cells," J Biol Chern. 273(33):20967-20971 (1998).
Nagy et al., "Stability of cytotoxic luteinizing hormone-releasing hormone conjugate (AN-152) containing doxorubicin 14-0-hemiglutarate in mouse and human serum in vitro: implications for the design of preclinical studies," Proc Natl Acad Sci US A. 97(2):829-834 (2000).
Neuberger et al., "A hapten-specific chimaeric IgE antibody with human physiological effector function," Nature. 314(6008):268-270 (1985).
Ngan et al., "Proto-oncogenes and p53 protein expression in normal cervical stratified squamous epithelium and cervical intra-epithelial neoplasia," Eur J Cancer. 35(10):1546-1550 1(1999).
Nicola et al., "Neutralizing and nonneutralizing monoclonal antibodies to the human granulocyte-macrophage colony-stimulating factor receptor alpha-chain," Blood. 82(6):1724-31 (1993).
Norderhaug et al., "Versatile vectors for transient and stable expression of recombinant antibody molecules in mammalian cells," J Immunol Methods. 204(1):77-87 (1997).
Orlandi et al., "Cloning immunoglobulin variable domains for expression by the polymerase chain reaction," Proc Natl Acad Sci US A. 86(10):3833-3837 (1989).
Patel et al., "Colony-stimulating factor-1 receptor inhibitors for the treatment of cancer and inflammatory disease," Curr Top Med Chem. 9(7):599-610 (2009).
Paul, Structure and funtcion of immunoglobulins, Fundamental Immunology, 3rd Ed., Raven Press, 292-295 (1993).
Paulus et al., "Colony-stimulating factor-1 antibody reverses chemoresistance in human MCF7 breast cancer xenografts," Cancer Res. 66(8):4349-4356 (2006).
Pixley et al., "CSF-1 regulation of the wandering macrophage: complexity in action," Trends Cell Biol. 14(11):628-638 (2004).
Pollard, "Role of colony-stimulating factor-1 in reproduction and development," Mol Reprod Dev. 46(1):54-60 (1997).
Pollard, "Tumour-educated macrophages promote tumour progression and metastasis," Nat Rev Cancer. 4(1):71-78 (2004).
Queen et al., "A humanized antibody that binds to the interleukin 2 receptor," Proc Natl Acad Sci US A. 86(24):10029-10033 (1989).
Rabello et al., "CSF1 gene associated with aggressive periodontitis in the Japanese population," Biochem Biophys Res Commun. 347(3):791-796 (2006).
Ridge et al., "FMS mutations in myelodysplastic, leukemic, and normal subjects," Proc Natl Acad Sci US A. 87(4):1377-1380 (1990).
Riechmann et al., "Reshaping human antibodies for therapy," Nature. 332(6162): 323-327 (1988).
Ries et al. (2014). "Targeting tumor-associated macrophages with anti-CSF-1R antibody reveals a strategy for cancer therapy," Cancer Cell, 25(6):846-59.
Ritchlin et al., "Mechanisms ofTNF-alpha-and RANKL-mediated osteoclastogenesis and bone resorption in psoriatic arthritis," J Clin Invest. 111(6):821-831 (2003).
Roggia et al., "Role of TNF-alpha producing T-cells in bone loss induced by estrogen deficiency," Minerva Med. 95(2):125-132 (2004).
Roth et al., "The biology of CSF-1 and its receptor," Curr Top Microbiol Immunol. 181:141-167 (1992).
Roussel et al., "Mouse NIH 3T3 cells expressing human colony-stimulating factor 1 (CSF-1) receptors overgrow in serum-free medium containing human CSF-1 as their only growth factor," Proc Natl Acad Sci US A. 86(20):7924-7927 (1989).
Roussel et al., "Transforming potential of the c-fms proto-oncogene (CSF-1 receptor)," Nature. 325(6104):549-552 (1987).
Saitoh et al., "Clinical significance of increased plasma concentration of macrophage colony-stimulating factor in patients with angina pectoris," J Am Coll Cardiol. 35(3):655-665 (2000).
Sawada et al., "Activation and proliferation of the isolated microglia by colony stimulating factor-1 and possible involvement of protein kinase C," Brain Res. 509(1):119-124 (1990).

(56) References Cited

OTHER PUBLICATIONS

Schlaeger et al., "Transient gene expression in mammalian cells grown in serum-free suspension culture," Cytotechnology. 30(1-3):71-83 (1999).

Schlaeger, "The protein hydrolysate, Primatone RL, is a cost-effective multiple growth promoter of mammalian cell culture in serum-containing and serum-free media and displays anti-apoptosis properties," J Immunol Methods. 194(2):191-199 (1996).

Scholl et al., "Anti-colony-stimulating factor-1 antibody staining in primary breast adenocarcinomas correlates with marked inflammatory cell infiltrates and prognosis," J Natl Cancer Inst. 86(2):120-126 (1994).

Shadduck et al., "Paradoxical stimulation of normal and leukemic rat hematopoiesis by monoclonal antibody to CSG-1 receptor," Experimental Hematology 24:314-317, (1996).

Sherr et al., "Inhibition of colony-stimulating factor-1 activity by monoclonal antibodies to the human CSF-1 receptor," Blood. 73(7):1786-93 (1989).

Sherr et al., "The c-fms proto-oncogene product is related to the receptor for the mononuclear phagocyte growth factor, CSF-1," Cell. 41(3):665-676 (1985).

Stanley et al., "Biology and action of colony-stimulating factor-1 ," Mol Reprod Dev. 46(1):4-10 (1997).

Stanley et al., "The biology and action of colony stimulating factor-1," Stem Cells. 12(Suppl 1):15-25 (1994).

Stanley et al., "CSF-1-A monoclonal phagocyte lineage-specific hemopoietic growth factor," Journal of Cellular Biochemistry 21(2):151-159, (1983).

Stoch et al., "Bone loss in men with prostate cancer treated with gonadotropin-releasing hormone agonists," J Clin Endocrinol Metab. 86(6):2787-2791 (2001).

Sudo, T. et al., "Functional hierarchy of c-kit and c-fms in intramarrow production of CFU-M" Oncogene 11(12):2469-2476 (Dec. 21, 1995).

Tanaka et al., "Macrophage colony-stimulating factor is indispensable for both proliferation and differentiation of osteoclast progenitors," J Clin Invest. 91(1):257-263 (1993).

Taylor et al., "FMS receptor for M-CSF (CSF-1) is sensitive to the kinase inhibitor imatinib and mutation of Asp-802 to Val confers resistance," Oncogene pp. 1-5, (2005).

Thommesen et al., "Lysine 322 in the human IgG3 C(H)2 domain is crucial for antibody dependent complement activation," Mol Immunol. 37(16):995-1004 (2000).

Torgov et al., "Generation of an intensely potent anthracycline by a monoclonal antibody-beta-Qalactosidase conjugate," Bioconjugate Chem. 16(3):717-721 (2005).

van Dijk et al., "Human antibodies as next generation therapeutics," Curr Opin Chem Biol. 5(4):368-374(2001).

Vessella et al., "Targeting factors involved in bone remodeling as treatment strategies in prostate cancer bone metastasis," Clin Cancer Res. 12(20 Pt 2):6285s-6290s (2006).

Vitetta et al., "Redesigning nature's poisons to create anti-tumor reagents," Science. 238(4830): 1098-1104 (1987).

Wang et al., "Identification of the ligand-binding regions in the macrophage colony-stimulating factor receptor extracellular domain," Mol Cell Biol. 13(9):5348-59 (1993).

Weir et al., "Colony stimulating factor-1 plays a role in osteoclast formation and function in bone resorption induced by parathyroid hormone and parathyroid hormone-related protein," Journal of Bone and Mineral 11(10)1474-1481 (1996).

Werner et al., "Appropriate mammalian expression systems for biopharmaceuticals," Arzneimittelforschung. 48(8):870-880 (1998).

West et al., "A landscape effect in tenosynovial giant-cell tumor from activation of CSF1 EK expression by a translocation in a minority of tumor cells," Proc Natl Acad Sci U S A. 103(3):690-695 (2006).

Written Opinion dated Nov. 18, 2014, for PCT Application No. PCT/EP2014/069451, filed on Sep. 11, 2014, six pages.

Written Opinion dated Sep. 1, 2011, for PCT Application No. PCT/EP2011/053213, filed on Mar. 3, 2011, seven pages.

Yang et al., "The relationship between point mutation and abnormal expression of c-fms oncogene in hepatocellular carcinoma," Hepatobiliary Pancreat Dis Int. 3(1):86-89 (2004).

Yeung et al., "Proteomic approaches to the analysis of early events in colony-stimulating factor-1 signal transduction," Mol Cell Proteomics. 2(11):1143-1155 (2003).

Zheng et al., "Membrane-bound macrophage colony-stimulating factor and its receptor play adhesion molecule-like roles in leukemic cells," Leuk Res. 24(5):375-383 (2000).

Zins et al., "Colon cancer cell-derived tumor necrosis factor-alpha mediates the tumor growth-promoting response in macrophages by up-regulating the colony-stimulating factor-1 pathway," Cancer Res. 67(3):1038-1045 (2007).

Caldas, C. et al. "Humanization of the Anti-CD18 Antibody 6.7: An Unexpected Effect of a Framework Residue in Binding to Antigen," *Mol. Immunol.* 39:941-952, (2003).

Sapi, E. et. al. "Effect of All-trans-Retinoic Acid on c-fms Proto-Oncogene [Colony-Stimulating Factor 1 (CSF-1) Receptor] Expression and CSF-1-Induced Invasion and Anchorage-Independent Growth of Human Breast Carcinoma Cells," *Cancer Res.* 59:5578-5585 (Nov. 1, 1999).

Shumlan, T. et al. "An Antibody Reactive With Domain 4 Of The Platelet-Derived Growth Factor β Receptor Allows BB Binding While Inhibiting Proliferation By Impairing Receptor Dimerization," *The Journal Of Biological Chemistry* 272(28):17400-17404, (Jul. 11, 1997).

Strausberg, R.L. et al. Colony Stimulation Factor 1 Receptor [*Homo Sapiens*] Accession No. AAH47521 (Aug. 7, 2008), 18 pages.

Yuzawa, S. et al. "Structural Basis For Activation Of The Receptor Tyrosine Kinase KIT By Stem Cell Factor," *Cell* 130(2):323-334, (Jul. 27, 2007).

U.S. Appl. No. 15/849,743, filed Dec. 21, 2017, for Dimoudis et al.
U.S. Appl. No. 15/686,834, filed Aug. 25, 2017, for Hoves et al.
U.S. Appl. No. 15/404,987, filed Jan. 12, 2017, for Hoves et al.
U.S. Appl. No. 15/875,530, filed Jan. 19, 2018, for Dimoudis et al.
U.S. Appl. No. 15/934,686, filed Mar. 12, 2018, for Fertig et al.
U.S. Appl. No. 15/947,647, filed Dec. 6, 2017, for Hoves et al.
U.S. Appl. No. 15/957,374, filed Apr. 19, 2018, for Hoves et al.

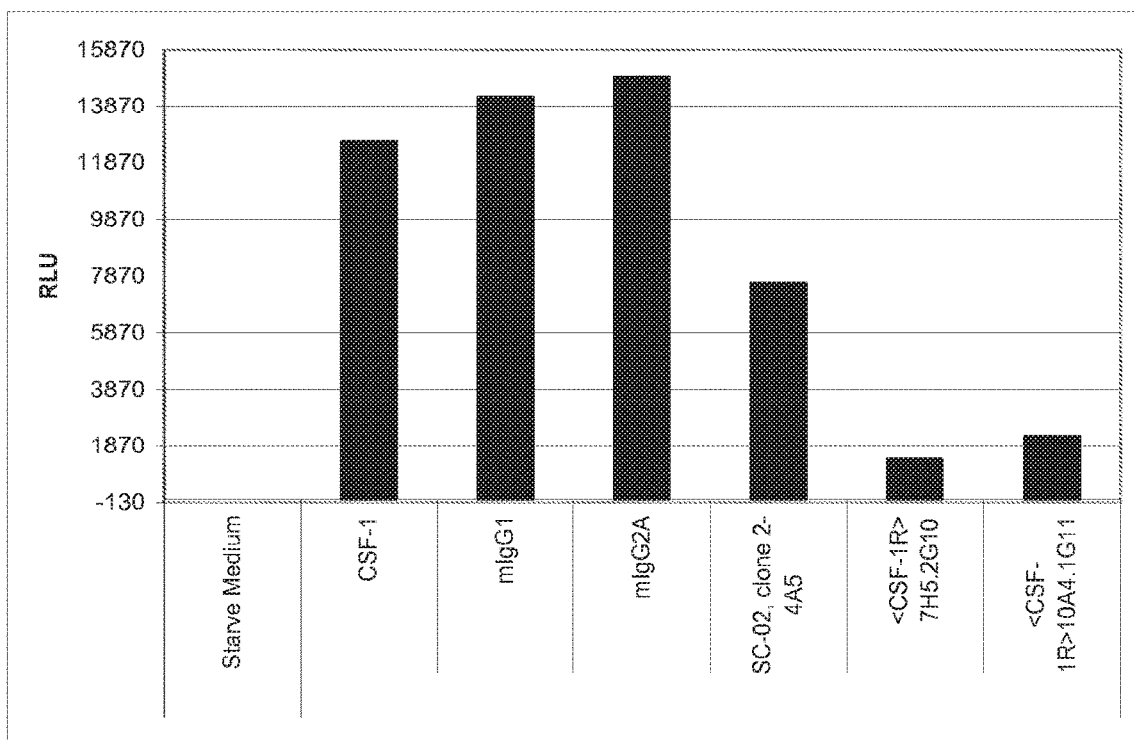

ANTIBODIES AGAINST HUMAN CSF-1R AND USES THEREOF

CROSS-REFERENCE TO RELATED APPLICATIONS

This application is a Divisional of U.S. patent application Ser. No. 14/642,101, filed Mar. 9, 2015, which is a Divisional of U.S. patent application Ser. No. 13/582,964, internationally filed Mar. 3, 2011, now patented as U.S. Pat. No. 9,169,323, issued Oct. 27, 2015, which is a National Phase application under 35 U.S.C. § 371 of International Application No. PCT/EP2011/053214, filed on Mar. 3, 2011, which claims the benefit of European Patent Application No. 10 002 268.0, filed on Mar. 5, 2010, the entire disclosures of which are expressly incorporated by reference herein.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392029711SEQLIST.txt, date recorded: Oct. 3, 2016, size: 41 KB).

FIELD OF THE INVENTION

The present invention relates to antibodies against human CSF-1R (CSF-1R antibody), methods for their production, pharmaceutical compositions containing said antibodies, and uses thereof.

BACKGROUND OF THE INVENTION

The CSF-1 receptor (CSF-1R; synonyms: M-CSF receptor, Macrophage colonystimulating factor 1 receptor, EC 2.7.10.1, Fns proto-oncogene, c-fms, Swiss Prot P07333, CD115) is known since 1986 (Coussens, L., et al., Nature 320 (1986) 277-280). CSF-1R is a growth factor and encoded by the c-fms proto-oncogene (reviewed e.g. in Roth, P., and Stanley, E. R., Curr. Top. Microbiol. Immunol. 181 (1992) 141-67).

CSF-1R is the receptor for M-CSF (macrophage colony stimulating factor, also called CSF-1) and mediates the biological effects of this cytokine (Sherr, C. J., et al., Cell 41 (1985) 665-676). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cb1 and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by repeated Ig domains in the extracellular portion of the receptor. The intracellular protein tyrosine kinase domain is interrupted by a unique insert domain that is also present in the other related RTK class III family members that include the platelet derived growth factor receptors (PDGFR), stem cell growth factor receptor (c-Kit) and fms-like cytokine receptor (FLT3). In spite of the structural homology among this family of growth factor receptors, they have distinct tissue-specific functions. CSF-1R is mainly expressed on cells of the monocytic lineage and in the female reproductive tract and placenta. In addition expression of CSF-1R has been reported in Langerhans cells in skin, a subset of smooth muscle cells (Inaba, T., et al., J. Biol. Chem. 267 (1992) 5693-5699), B cells (Baker, A. H., et al., Oncogene 8 (1993) 371-378) and microglia (Sawada, M., et al., Brain Res. 509 (1990) 119-124).

The main biological effects of CSF-1R signaling are the differentiation, proliferation, migration, and survival of hematopoietic precursor cells to the macrophage lineage (including osteoclast). Activation of CSF-1R is mediated by its ligand, M-CSF. Binding of M-CSF to CSF-1R induces the formation of homodimers and activation of the kinase by tyrosine phosphorylation (Stanley, E. R., et al., Mol. Reprod. Dev. 46 (1997) 4-10). Further signaling is mediated by the p85 subunit of PI3K and Grb2 connecting to the PI3K/AKT and Ras/MAPK pathways, respectively. These two important signaling pathways can regulate proliferation, survival and apoptosis. Other signaling molecules that bind the phosphorylated intracellular domain of CSF-1R include STAT1, STAT3, PLCy, and Cb1 (Bourette, R. P., Rohrschneider, L. R., Growth Factors 17 (2000) 155-166).

CSF-1R signaling has a physiological role in immune responses, in bone remodeling and in the reproductive system. The knockout animals for either M-CSF-1 (Pollard, J. W., Mol. Reprod. Dev. 46 (1997) 54-61) or CSF-1R (Dai, X. M., et al., Blood 99 (2002) 111-120) have been shown to have osteopetrotic, hematopoietic, tissue macrophage, and reproductive phenotypes consistent with a role for CSF-1R in the respective cell types.

Sherr, C. J., et al., Blood 73 (1989) 1786-1793 relates to some antibodies against CSF-1R that inhibit the CSF-1 activity (see Sherr, C. J., et al., Blood 73 (1989) 1786-1793). Ashmun, R. A., et al., Blood 73 (1989) 827-837 relates to CSF-1R antibodies. Lenda, D., et al., Journal of immunology 170 (2003) 3254-3262 relates to reduced macrophage recruitment, proliferation, and activation in CSF-1-deficient mice results in decreased tubular apoptosis during renal inflammation. Kitaura, H., et al., Journal of dental research 87 (2008) 396-400 refers to an anti-CSF-1 antibody which inhibits orthodontic tooth movement. WO 2001/030381 mentions CSF-1 activity inhibitors including antisense nucleotides and antibodies while disclosing only CSF-1 antisense nucleotides. WO 2004/045532 relates to metastases and bone loss prevention and treatment of metastatic cancer by a M-CSF antagonist disclosing as antagonist anti-CSF-1-antibodies only. WO 2005/046657 relates to the treatment of inflammatory bowel disease by anti-CSF-1-antibodies. US 2002/0141994 relates to inhibitors of colony stimulating factors. WO 2006/096489 relates to the treatment of rheumatoid arthritis by anti-CSF-1-antibodies.

WO 2009/026303 and WO 2009/112245 relate to anti-CSF-1R antibodies.

SUMMARY OF THE INVENTION

The invention comprises an antibody binding to human CSF-1R, characterized in binding to same epitope as the deposited antibody DSM ACC2922.

In one embodiment the antibody is characterized in comprising as heavy chain variable domain CDR3 region a CDR3 region of SEQ ID NO: 1, SEQ ID NO: 9, or SEQ ID NO: 17.

In one embodiment the antibody is characterized in that
a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
b) the heavy chain variable domain comprises a CDR3 region of SEQ ID NO: 9, a CDR2 region of SEQ ID NO: 10, and a CDR1 region of SEQ ID NO: II, and the light chain variable domain comprises a CDR3 region of SEQ ID NO:12, a CDR2 region of SEQ ID NO: 13, and a CDR1 region of SEQ ID NO: 14; or
c) the heavy chain variable domain comprises a CDR3 region of SEQ ID NO: 17, a CDR2 region of SEQ ID NO: 18, and a CDR1 region of SEQ ID NO: 19, and i the light chain variable domain comprises a CDR3 region of SEQ ID NO:20, a CDR2 region of SEQ ID NO: 21, and a CDR1 region of SEQ ID NO: 22; or
d) a CDR grafted, humanized or T cell epitope depleted antibody variant of the antibodies of a), b) or c).

In one embodiment the antibody is characterized in comprising
a) the amino acid sequence of the heavy chain variable domain is SEQ ID NO: 7, and the amino acid sequence of the light chain variable domain is SEQ ID NO:8, or
b) the amino acid sequence of the heavy chain variable domain is SEQ ID NO: 15, and the amino acid sequence of the light chain variable domain is SEQ ID NO:16, or
c) the amino acid sequence of the heavy chain variable domain is SEQ ID NO: 23, and the amino acid sequence of the light chain variable domain is SEQ ID NO:24 or
d) a CDR grafted, humanized or T cell epitope depleted antibody variant of the antibodies of a), b) or c).

In one embodiment the antibody binding to human CSF-1R and being characterized by the above mentioned amino acid sequences and amino acid sequence fragments is of human IgG1 subclass or is of human IgG4 subclass.

A further embodiment of the invention is a pharmaceutical composition comprising an antibody according to the invention.

The invention further comprises a pharmaceutical composition characterized in comprising the antibody binding to human CSF-1R being characterized by the above mentioned epitope binding properties or alternatively by the above mentioned amino acid sequences and amino acid sequence fragments.

The invention further comprises the use an of an antibody characterized characterized in comprising the antibody binding to human CSF-1R being characterized by the above mentioned epitope binding properties or alternatively by the above mentioned amino acid sequences and amino acid sequence fragments for the manufacture of a pharmaceutical composition.

The invention further comprises the use of an antibody characterized in comprising the antibody binding to human CSF-1R being characterized by the above mentioned epitope binding properties or alternatively by the above mentioned amino acid sequences and amino acid sequence fragments for the treatment of a CSF-1R mediated diseases.

The invention further comprises the use of an antibody characterized in comprising the antibody binding to human CSF-1R being characterized by the above mentioned epitope binding properties or alternatively by the above mentioned amino acid sequences and amino acid sequence fragments for the treatment of cancer.

The invention further comprises the use of an antibody characterized in comprising the antibody binding to human CSF-1R being characterized by the above mentioned epitope binding properties or alternatively by the above mentioned amino acid sequences and amino acid sequence fragments for the treatment of bone loss.

The invention further comprises the of an antibody characterized in comprising the antibody binding to human CSF-1R being characterized by the above mentioned epitope binding properties or alternatively by the above mentioned amino acid sequences and amino acid sequence fragments for the prevention or treatment of metastasis.

The invention further comprises the of an antibody characterized in comprising the antibody binding to human CSF-1R being characterized by the above mentioned epitope binding properties or alternatively by the above mentioned amino acid sequences and amino acid sequence fragments for treatment of inflammatory diseases.

One aspect of the invention is an antibody binding to human CSF-1R, characterized in comprising as heavy chain variable domain CDR3 region a CDR3 region of SEQ ID NO: 1, SEQ ID NO: 9, or SEQ ID NO: 17.

Another aspect of the invention is an antibody binding to human CSF-1R, characterized in that
a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14; or
c) the heavy chain variable domain comprises a CDR3 region of SEQ ID NO: 17, a CDR2 region of SEQ ID NO: 18, and a CDR1 region of SEQ ID NO: 19, and i the light chain variable domain comprises a CDR3 region of SEQ ID NO:20, a CDR2 region of SEQ ID NO: 21, and a CDR1 region of SEQ ID NO: 22; or
d) a CDR grafted, humanized or T cell epitope depleted antibody variant of the antibodies of a), b) or c).

In one embodiment the antibody is characterized in comprising
a) the amino acid sequence of the heavy chain variable domain is SEQ ID NO: 7, and the amino acid sequence of the light chain variable domain is SEQ ID NO:8, or
b) the amino acid sequence of the heavy chain variable domain is SEQ ID NO: 15, and the amino acid sequence of the light chain variable domain is SEQ ID NO:16, or
c) the amino acid sequence of the heavy chain variable domain is SEQ ID NO: 23, and the amino acid sequence of the light chain variable domain is SEQ ID NO:24, or
d) a CDR grafted, humanized or T cell epitope depleted antibody variant of the antibodies of a), b) or c).

In one aspect of the invention the antibodies according to the invention bind to human CSF-1R with an affinity of at least $10^{-8}$ mol/l to $10^{-12}$ mol/l.

In one aspect of the invention the antibodies according to the invention is a humanized antibody.

A further embodiment of the invention is a nucleic acid encoding a heavy chain variable domain and/or a light chain variable domain of an antibody according to the invention. Preferably the nucleic acid encodes a heavy chain of an antibody binding to human CSF-1R, characterized in comprising as heavy chain CDR3 region a CDR3 region of SEQ ID NO: 1, SEQ ID NO: 9, or SEQ ID NO: 17.

A further embodiment of the invention is a nucleic acid encoding an antibody according to the invention characterized in that
   a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
   b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14; or
   c) the heavy chain variable domain comprises a CDR3 region of SEQ ID NO: 17, a CDR2 region of SEQ ID NO: 18, and a CDR1 region of SEQ ID NO: 19, and i the light chain variable domain comprises a CDR3 region of SEQ ID NO:20, a CDR2 region of SEQ ID NO: 21, and a CDR1 region of SEQ ID NO: 22: or
   d) a CDR grafted, humanized or T cell epitope depleted antibody variant of the antibodies of a), b) or c).

The invention further provides expression vectors containing nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant.

The invention further comprises the antibody obtainable by such a recombinant method.

Antibodies according to the invention show benefits for patients in need of a CSF-1R targeting therapy. The antibodies according to the invention have new and inventive properties causing a benefit for a patient suffering from a tumor disease, especially suffering from cancer.

The invention further provides a method for treating a patient suffering from cancer, comprising administering to a patient diagnosed as having such a disease (and therefore being in need of such a therapy) an effective amount of an antibody binding to human CSF-1R according to the invention. The antibody is administered preferably in a pharmaceutical composition.

A further embodiment of the invention is a method for the treatment of a patient suffering from cancer characterized by administering to the patient an antibody according to the invention.

The invention further comprises the use of an antibody according to the invention for the treatment of a patient suffering from cancer and for the manufacture of a pharmaceutical composition according to the invention. In addition, the invention comprises a method for the manufacture of a pharmaceutical composition according to the invention.

The invention further comprises a pharmaceutical composition comprising an antibody according to the invention, optionally together with a buffer and/or an adjuvant useful for the formulation of antibodies for pharmaceutical purposes.

The invention further provides pharmaceutical compositions comprising an antibody according to the invention in a pharmaceutically acceptable carrier. In one embodiment, the pharmaceutical composition may be included in an article of manufacture or kit.

BRIEF DESCRIPTION OF THE FIGURES

FIG. 1 Growth inhibition of BeWo tumor cells in 3D culture under treatment with different anti-CSF-1R monoclonal antibodies at a concentration of 10 µg/ml.
   X axis: viability mean relative light units (RLU) corresponding to the ATP-content of the cells (CellTiterGlo assay).
   Y axis: tested probes: Minimal Medium (0.5% FBS), mouse IgG1 (mIgG1, 10 µg/ml), mouse IgG2a (mIgG2a 10 µg/ml), CSF-1 only, <CSF-1R>7H5.2G10, <CSF-1R>10A4.1G11, and SC-02, clone 2-4A5.
   Highest inhibition of CSF-1 induced growth was observed with the anti-CSF-1R antibodies according to the invention.

DETAILED DESCRIPTION OF EMBODIMENTS OF THE INVENTION

I. Definitions

The term "antibody" encompasses the various forms of antibodies including but not being limited to whole antibodies, antibody fragments, humanized antibodies, chimeric antibodies, T cell epitope depleted antibodies, and further genetically engineered antibodies as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Houston, J. S., Methods in Enzymol. 203 (1991) 46-88). In addition, antibody fragments comprise single chain polypeptides having the characteristics of a $V_H$ domain binding to CSF-1R, namely being able to assemble together with a $V_L$ domain, or of a $V_L$ domain binding to CSF-1R, namely being able to assemble together with a $V_H$ domain to a functional antigen binding site and thereby providing the property.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "CDR-grafted variant" as used within the current application denotes a variable domain of an antibody comprising complementary determining regions (CDRs or hypervariable regions) from one source or species and framework regions (FRs) from a different source or species, usually prepared by recombinant DNA techniques. CDR-grafted variants of variable domains comprising murine CDRs and a human FRs are preferred.

The term "T-cell epitope depleted variant" as used within the current application denotes a variable domain of an antibody which was modified to remove or reduce immunogenicity by removing human T-cell epitopes (peptide sequences within the variable domains with the capacity to bind to MHC Class II molecules). By this method interactions between amino acid side chains of the variable domain and specific binding pockets with the MHC class II binding groove are identified. The identified immunogenic regions are mutated to eliminate immunogenicity. Such methods are described in general in, e.g., WO 98/52976.

The term "humanized variant" as used within the current application denotes a variable domain of an antibody, which is reconstituted from the complementarity determining regions (CDRs) of non-human origin, e.g. from a non-human species, and from the framework regions (FRs) of human origin, and which has been further modified in order to also reconstitute or improve the binding affinity and specificity of the original non-human variable domain. Such humanized variants are usually prepared by recombinant DNA techniques. The reconstitution of the affinity and specificity of the parent non-human variable domain is the critical step, for which different methods are currently used. In one method it is determined whether it is beneficial to introduce mutations, so called backmutations, in the non-human CDRs as well as in the human FRs. The suited positions for such backmutations can be identified e.g. by sequence or homology analysis, by choosing the human framework (fixed frameworks approach; homology matching or best-fit), by using consensus sequences, by selecting FRs from several different human mAbs, or by replacing non-human residues on the three dimensional surface with the most common residues found in human mAbs ("resurfacing" or "veneering").

The antibodies according to the invention include, in addition, such antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CSF-1R antibody can be preferably replaced with another amino acid residue from the same side chain family.

Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

The term "CSF-1R" as used herein refers to human CSF-1R (SEQ ID No: 31) CSF-1R (synonyms: CSF-1 receptor M-CSF receptor; Macrophage colony-stimulating factor 1 receptor, EC 2.7.10.1, Fms proto-oncogene, c-fms, Swiss Prot P07333, CD115,) is known since 1986 (Coussens, L., et al., Nature 320 (1986) 277-280). CSF-1R is a growth factor and encoded by the c-fms proto-oncogene (reviewed e.g. in Roth, P. and Stanley, E. R., Curr. Top. Microbiol. Immunol. 181 (1992) 141-67).

CSF-1R is the receptor for M-CSF (macrophage colony stimulating factor, also called CSF-1) and mediates the biological effects of this cytokine (Sherr, C. J., et al., Cell 41 (1985) 665-676). The cloning of the colony stimulating factor-1 receptor (also called c-fms) was described for the first time in Roussel, M. F., et al., Nature 325 (1987) 549-552. In that publication, it was shown that CSF-1R had transforming potential dependent on changes in the C-terminal tail of the protein including the loss of the inhibitory tyrosine 969 phosphorylation which binds Cb1 and thereby regulates receptor down regulation (Lee, P. S., et al., Embo J. 18 (1999) 3616-3628).

CSF-1R is a single chain, transmembrane receptor tyrosine kinase (RTK) and a member of the family of immunoglobulin (Ig) motif containing RTKs characterized by repeated Ig domains in the extracellular portion of the receptor. The intracellular protein tyrosine kinase domain is interrupted by a unique insert domain that is also present in the other related RTK class III family members that include the platelet derived growth factor receptors (PDGFR), stem cell growth factor receptor (c-Kit) and fms-like cytokine receptor (FLT3). In spite of the structural homology among this family of growth factor receptors, they have distinct tissue-specific functions. CSF-1R is mainly expressed on cells of the monocytic lineage and in the female reproductive tract and placenta. In addition expression of CSF-1R has been reported in Langerhans cells in skin, a subset of smooth muscle cells (Inaba, T., et al., J. Biol. Chem. 267 (1992) 5693-5699), B cells (Baker, A. H., et al., Oncogene 8 (1993) 371-378) and microglia (Sawada, M., et al., Brain Res. 509 (1990) 119-124).

As used herein, the terms "binding to human CSF-1R" or "that binds to human CSF-1R" or anti-CSF-1R" are used interchangeable and refer to an antibody specifically binding to the human CSF-1R antigen. The binding affinity is of KD-value of $1.0 \times 10^{-8}$ mol/l or lower at 35° C., preferably of a KD-value of $1.0 \times 10^{-9}$ mol/l or lower at 35° C. The binding affinity is determined with a standard binding assay at 35° C., such as surface plasmon resonance technique (Biacore®)) (see Example 4).

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and nonconformational epitopes are distinguished in that the binding to the former but not the latter is lost in the presence of denaturing solvents. Preferably an antibody according to the invention binds specifically to native but not to denatured CSF-1R.

The term "binding to the same epitope as the deposited antibody DSM ACC2922" as used herein refers to an anti-CSF-1R antibody of the invention that binds to the same epitope on CSF-1R to which the antibody <CSF-1R>7H5.2G10 (deposit no. DSM ACC2922) binds. The epitope binding property of an anti-CSF-1R antibody of the present invention may be determined using techniques known in the art. The CSF-1R antibody is measured by Surface Plasmon Resonance (SPR) at 25° C. in an in vitro competitive binding inhibition assay to determine the ability of the test antibody to inhibit binding of antibody <CSF-1R>7H5.2G10 (deposit no. DSM ACC2922) to CSF-1R. This can be investigated by a BIAcore assay (Pharmacia Biosensor AB, Uppsala, Sweden) as e.g. in Example 5. In Example 5 the percentage (%) of expected binding response of the CSF-1R antibody of the invention competing with the bound the antibody <CSF-1R>7H5.2G10 (deposit no. DSM ACC2922) is calculated by "100*relativeResponse(general_stability_early)/rMax", where rMax is calculated by "relativeResponse(general_stability_late)*antibody molecular weight/antigen molecular weight" as described in BIAcore assay epitope mapping instructions. A minimal binding response is also calculated from the pairs of identical antibody 1 and 2 (see Example 5). Thereof the obtained maximal value+50% is set as threshold for significant competition and thus significant binding to the same epitope (see Example 5 for antibody <CSF-1R>7H5.2G10 calculated threshold is 7+3.5=10.5). Thus an antibody binding to human CSF-1R, characterized in "binding to the same epitope as <CSF-1R>7H5.2G10 (deposit no. DSM ACC2922)" has a percentage (%) of expected binding response of lower than 10.5 (% expected binding response <10.5).

In one aspect the antibodies according to the invention compete with deposited antibody DSM ACC2922 for binding to human CSF-1R. Such binding competition may be determined using techniques known in the art. The CSF-1R antibody is measured at 25° C. by Surface Plasmon Resonance (SPR) in an in vitro competitive binding inhibition assay to determine the ability of the test antibody to inhibit binding of antibody <CSF-1R>7115.2G10 (deposit no. DSM ACC2922) to human CSF-1R. This can be investigated by a BIAcore assay (Pharmacia Biosensor AB, Uppsala, Sweden) as e.g. in Example 5.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat, E., A., et al., Sequences of Proteins of Immunological Interest, 5th ed., Public Health Service, National Institutes of Health, Bethesda, Md. (1991) and/or those residues from a "hypervariable loop".

The terms "nucleic acid" or "nucleic acid molecule", as used herein, are intended to include DNA molecules and RNA molecules. A nucleic acid molecule may be single-stranded or double-stranded, but preferably is double-stranded DNA.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CSF-1R antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

"Native antibodies" refer to naturally occurring immunoglobulin molecules with varying structures. For example, native IgG antibodies are heterotetrameric glycoprotcins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

II. Compositions and Methods

In one aspect, the invention is based, in part, on to same epitope as the deposited antibody DSM ACC2922. Antibodies of the invention are useful, e.g., for the diagnosis or treatment of cancer, of inflammatory diseases or of bone loss; or for the prevention or treatment of metastasis.

Exemplary Anti-CSF-1R Antibodies

In one aspect, the invention provides antibodies that bind to human CSF-1R. In certain embodiments, the anti-CSF-1R antibody is characterized in binding to same epitope as the deposited antibody DSM ACC2922.

Another aspect of the invention is an antibody binding to human CSF-1R, characterized in that
    a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
    b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14; or
    c) the heavy chain variable domain comprises a CDR3 region of SEQ ID NO: 17, a CDR2 region of SEQ ID NO: 18, and a CDR1 region of SEQ ID NO: 19, and i the light chain variable domain comprises a CDR3 region of SEQ ID NO:20, a CDR2 region of SEQ ID NO: 21, and a CDR1 region of SEQ ID NO: 22; or
    d) a CDR grafted, humanized or T cell epitope depleted antibody variant of the antibodies of a), b) or c).

Another aspect of the invention is an antibody binding to human CSF-1R, characterized in that
    a) the heavy chain variable domain comprises a CDR3 region of SEQ ID NO: 1, a CDR2 region of SEQ ID NO: 2, and a CDR1 region of SEQ ID NO:3, and the light chain variable domain comprises a CDR3 region of SEQ ID NO: 4, a CDR2 region of SEQ ID NO:5, and a CDR1 region of SEQ ID NO:6, or
    b) the heavy chain variable domain comprises a CDR3 region of SEQ ID NO: 9, a CDR2 region of SEQ ID NO: 10, and a CDR1 region of SEQ ID NO: 11, and the light chain variable domain comprises a CDR3 region of SEQ ID NO:12, a CDR2 region of SEQ ID NO: 13, and a CDR1 region of SEQ ID NO: 14; or
    c) the heavy chain variable domain comprises a CDR3 region of SEQ ID NO: 17, a CDR2 region of SEQ ID NO: 18, and a CDR1 region of SEQ ID NO: 19, and i the light chain variable domain comprises a CDR3 region of SEQ ID NO:20, a CDR2 region of SEQ ID NO: 21, and a CDR1 region of SEQ ID NO: 22; or
    d) a CDR grafted, humanized or T cell epitope depleted antibody variant of the antibodies of a), b) or c); and having one or more of the following properties (determined in assays as described in Example 2, 3, 4, 6, 7 and 8):
    the anti-CSF-1R antibody inhibits CSF-1 binding to CSF-1R with an IC50 of 75 ng/ml or lower, in one embodiment with an IC50 of 50 ng/ml or lower;
    the anti-CSF-1R antibody inhibits CSF-1-induced CSF-1R phosphorylation (in NIH3T3-CSF-1R recombinant cells) with an IC50 of 100 ng/ml or lower, in one embodiment with an IC50 of 50 ng/ml or lower;
    the anti-CSF-1R antibody inhibits the growth of recombinant NIH3T3 cells expressing human CSF-1R (SEQ ID No: 15) by 80% or more (as compared to the absence of antibody), preferably by 90% or more;
    the anti-CSF-1R antibody inhibits the growth of BeWo tumor cells (ATCC CCL-98) by 70% or more (at a antibody concentration of 10 μg/ml; and as compared to the absence of antibody), preferably by 80% or more; the anti-CSF-1R antibody inhibits macrophage differentiation. (In one embodiment the anti-CSF-1R antibody inhibits the survival of monocytes with an IC50 of 1.5 nM or lower, preferably with an IC50 of 1.0 nM or lower); or the anti-CSF-1R antibody is binding to human CSF-1R with a binding affinity of KD=$2.0 \times 10^{-9}$ mol/l or lower at 35° C.

In another aspect, an anti-CSF-1R antibody according to the invention comprises in the heavy chain variable domain (VH) sequence a) a CDR1H having an amino acid sequence identical to, or comprising 1, 2, or 3 amino acid residue substitutions relative to SEQ ID NO:3, SEQ ID NO:11 or SEQ ID NO:19, b) a CDR2H having an amino acid sequence identical to, or comprising 1, 2, or 3 amino acid residue substitutions relative to SEQ ID NO:2, SEQ ID NO:10 or SEQ ID NO:18, and c) a CDR3H having an amino acid sequence identical to, or comprising 1, 2, or 3 amino acid residue substitutions relative to SEQ ID NO:1. SEQ ID NO:9 or SEQ ID NO:17.

In certain embodiments, a heavy chain variable domain (VH) sequence comprising a) a CDR1H having an amino acid sequence identical to, or comprising 1, 2, or 3 amino acid residue substitutions relative to SEQ ID NO:3, SEQ ID NO: 11 or SEQ ID NO: 19, b) a CDR2H having an amino acid sequence identical to, or comprising 1, 2, or 3 amino acid residue substitutions relative to SEQ ID NO:2, SEQ ID NO:10 or SEQ ID NO:18, and c) a CDR3H having an amino acid sequence identical to, or comprising 1, 2, or 3 amino acid residue substitutions relative to SEQ ID NO:1, SEQ ID NO:9 or SEQ ID NO:17, contains substitutions (e.g., conservative substitutions), insertions, or deletions relative to the reference sequence, but an anti CSF-1R antibody comprising that sequence retains the ability to bind to CSF-1R.

In another aspect, an anti-CSF-1R antibody according to the invention comprises in the light chain variable domain (VL) sequence a) a CDR1L having an amino acid sequence identical to, or comprising 1, 2, or 3 amino acid residue substitutions relative to SEQ ID NO:6, SEQ ID NO:14 or SEQ ID NO:22, b) a CDR2L having an amino acid sequence identical to, or comprising 1, 2, or 3 amino acid residue substitutions relative to SEQ 1D NO:5, SEQ ID NO:13 or SEQ ID NO:21, and c) a CDR3L having an amino acid sequence identical to, or comprising 1, 2, or 3 amino acid residue substitutions relative to SEQ ID NO:4, SEQ ID NO: 12 or SEQ ID NO:20.

In certain embodiments, a light chain variable domain (VL) sequence comprising a) a CDR1L having an amino acid sequence identical to, or comprising 1, 2, or 3 amino acid residue substitutions relative to SEQ ID NO:6, SEQ ID NO: 14 or SEQ ID NO:22, b) a CDR2L having an amino acid sequence identical to, or comprising 1, 2, or 3 amino acid residue substitutions relative to SEQ ID NO:5, SEQ ID NO:13 or SEQ ID NO:21, and c) a CDR3L having an amino acid sequence identical to, or comprising 1, 2, or 3 amino acid residue substitutions relative to SEQ ID NO:4, SEQ ID NO:12 or SEQ ID NO:20, contains substitutions (e.g., conservative substitutions), insertions, or deletions relative to the reference sequence, but an anti CSF-1R antibody comprising that sequence retains the ability to bind to CSF-1R.

In another aspect, an anti-CSF-1R antibody according to the invention
comprises in the heavy chain variable domain (VH) sequence a) a CDR1H having an amino acid sequence identical to, or comprising 1, 2, or 3 amino acid residue substitutions relative to SEQ ID NO:3, b) a CDR2H having an amino acid sequence identical to, or comprising 1, 2, or 3 amino acid residue substitutions relative to SEQ ID NO:2, and c) a CDR3H having an amino acid sequence identical to, or comprising 1, 2, or 3 amino acid residue substitutions relative to SEQ ID NO:1, and comprises in the light chain variable domain (VL) sequence d) a having an amino acid sequence identical to, or comprising 1, 2, or 3 amino acid residue substitutions relative to SEQ ID NO:6, e) a CDR2L having an amino acid sequence identical to, or comprising 1, 2, or 3 amino acid residue substitutions relative to SEQ ID NO:5, and f) a CDR3L having an amino acid sequence identical to, or comprising 1, 2, or 3 amino acid residue substitutions relative to SEQ ID NO:4; or comprises in the heavy chain variable domain (VH) sequence a) a CDR1H having an amino acid sequence identical to, or comprising 1, 2, or 3 amino acid residue substitutions relative to SEQ ID NO: 11, b) a CDR2H having an amino acid sequence identical to, or comprising 1, 2, or 3 amino acid residue substitutions relative to SEQ ID NO: 10, and c) a CDR3H having an amino acid sequence identical to, or comprising 1, 2, or 3 amino acid residue substitutions relative to SEQ ID NO:9, and comprises in the light chain variable domain (VL) sequence d) a CDR1L having an amino acid sequence identical to, or comprising 1, 2, or 3 amino acid residue substitutions relative to SEQ ID NO:14, e) a CDR2L having an amino acid sequence identical to, or comprising 1, 2, or 3 amino acid residue substitutions relative to SEQ ID NO:13, and f) a CDR3L having an amino acid sequence identical to, or comprising 1, 2, or 3 amino acid residue substitutions relative to SEQ ID NO: 12; or comprises in the heavy chain variable domain (VH) sequence a) a CDR1H having an amino acid sequence identical to, or comprising 1, 2, or 3 amino acid residue substitutions relative to SEQ ID NO: 19, b) a CDR2H having an amino acid sequence identical to, or comprising 1, 2, or 3 amino acid residue substitutions relative to SEQ ID NO: 18, and c) a CDR3H having an amino acid sequence identical to, or comprising 1, 2, or 3 amino acid residue substitutions relative to SEQ ID NO: 17, and comprises in the light chain variable domain (VL) sequence d) a CDR1L having an amino acid sequence identical to, or comprising 1, 2, or 3 amino acid residue substitutions relative to SEQ ID NO:22, e) a CDR2L having an amino acid sequence identical to, or comprising 1, 2, or 3 amino acid residue substitutions relative to SEQ ID NO:21, and f) a CDR3L having an amino acid sequence identical to, or comprising 1, 2, or 3 amino acid residue substitutions relative to SEQ ID NO:20.

In another aspect, an anti-CSF-1R antibody according to the invention
comprises in the heavy chain variable domain (VH) sequence a) a CDR1H having an amino acid sequence identical to, or comprising 1, 2, or 3 amino acid residue substitutions relative to SEQ ID NO:3, b) a CDR2H having an amino acid sequence identical to, or comprising 1, 2, or 3 amino acid residue substitutions relative to SEQ ID NO:2, and c) a CDR3H having an amino acid sequence identical to, or comprising 1, 2, or 3 amino acid residue substitutions relative to SEQ ID NO: 1, and comprises in the light chain variable domain (VL) sequence d) a CDR1L having an amino acid sequence identical to, or comprising 1, 2, or 3 amino acid residue substitutions relative to SEQ ID NO:6, e) a CDR2L having an amino acid sequence identical to, or comprising 1, 2, or 3 amino acid residue substitutions relative to SEQ ID NO:5, and f) a CDR3L having an amino acid sequence identical to, or comprising 1, 2, or 3 amino acid residue substitutions relative to SEQ ID NO:4; or comprises in the heavy chain variable domain (VH) sequence a) a CDR1H having an amino acid sequence identical to, or comprising 1, 2, or 3 amino acid residue substitutions relative to SEQ ID NO: 11, b) a CDR2H having an amino acid sequence identical to, or comprising 1, 2, or 3 amino acid residue substitutions relative to SEQ ID NO: 10, and c) a CDR3H having an amino acid sequence identical to, or comprising 1, 2, or 3 amino acid residue substitutions relative to SEQ ID NO:9, and comprises in the light chain variable domain (VL) sequence d) a CDR1L having an amino acid sequence identical to, or comprising 1, 2, or 3 amino acid residue substitutions relative to SEQ ID NO:14, e) a CDR2L having an amino acid sequence identical to, or comprising 1, 2, or 3 amino acid residue substitutions relative to SEQ ID NO:13, and f) a CDR3L having an amino acid sequence identical to, or comprising 1, 2, or 3 amino acid residue substitutions relative to SEQ ID NO: 12; or comprises in the heavy chain variable domain (VH) sequence a) a CDR1H having an amino acid sequence identical to, or comprising 1, 2, or 3 amino acid residue substitutions relative to SEQ ID NO: 19, b) a CDR2H having an amino acid sequence identical to, or comprising 1, 2, or 3 amino acid residue substitutions relative to SEQ ID NO: 18, and c) a CDR3H having an amino acid sequence identical to, or comprising 1, 2, or 3 amino acid residue substitutions relative to SEQ ID NO:17, and comprises in the light chain variable domain (VL) sequence d) a CDR1L having an amino acid sequence identical to, or comprising 1, 2, or 3 amino acid residue substitutions relative to SEQ ID NO:22, e) a CDR2L having an amino acid sequence identical to, or comprising 1, 2, or 3 amino acid residue substitutions relative to SEQ ID NO:21, and f) a CDR3L having an amino acid sequence identical to, or comprising 1, 2, or 3 amino acid residue substitutions relative to SEQ ID NO:20; and the anti-CSF-1R antibody has one or more of the following properties (determined in assays as described in Example 2, 3, 4, 6, 7 and 8):

the anti-CSF-1R antibody inhibits CSF-1 binding to CSF-1R with an IC50 of 75 ng/ml or lower, in one embodiment with an IC50 of 50 ng/ml or lower;

the anti-CSF-1R antibody inhibits CSF-1-induced CSF-1R phosphorylation (in NIH3T3-CSF-1R recombinant cells) with an IC50 of 100 ng/ml or lower, in one embodiment with an IC50 of 50 ng/ml or lower;

the anti-CSF-1R antibody inhibits the growth of recombinant NIH3T3 cells expressing human CSF-1R (SEQ ID No: 15) by 80% or more (as compared to the absence of antibody), preferably by 90% or more;

the anti-CSF-1R antibody inhibits the growth of BeWo tumor cells (ATCC CCL-98) by 70% or more (at a antibody concentration of 10 g/ml; and as compared to the absence of antibody), preferably by 80% or more;

the anti-CSF-1R antibody inhibits macrophage differentiation. (In one embodiment the anti-CSF-1R antibody inhibits the survival of monocytes with an IC50 of 1.5 nM or lower, preferably with an IC50 of 1.0 nM or lower); or the anti-CSF-1R antibody is binding to human CSF-1R with a binding affinity of KD=$2.0\times10^{-9}$ mol/l or lower at 35° C.

Recombinant Methods and Compositions

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S.C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified, or substantially pure form. Purification is performed in order to eliminate other cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J., Christensen, K., in Cytotechnology 30 (1999) 71-83, and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Nucleic acid molecules encoding amino acid sequence variants of anti-CSF-1R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CSF-1R antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described e.g. by Boakle, R. J., et al., Nature 282 (1979) 742-743, Lukas, T. J., et al., J. Immunol. 127 (1981) 2555-2560, Brunhouse, R., Cenbra, J., J., Mol. Immunol. 16 (1979) 907-917, Burton, D. R., et al., Nature 288 (1980) 338-344, Thommesen, J. E., et al., Mol. Immunol. 37 (2000) 995-1004, Idusogie, E. E., et al., J. Immunol. 164 (2000) 4178-4184, Hezareh, M., et al., J. Virology 75 (2001) 12161-12168, Morgan, A., et al., Immunology 86 (1995) 319-324, EP 0307434. Such binding sites are e.g. L234, L235, D270, N297, E318. K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Mostly preferred are the human heavy chain constant regions of SEQ ID NO:27 (human IgG1 subclass), SEQ ID NO: 28 (human IgG subclass with mutations L234A and L235A), SEQ ID NO:29 human IgG4 subclass), or SEQ ID NO:30 (human IgG4 subclass with mutation S228P).

In one embodiment the antibody according to the invention is characterized in that the constant chains are of human origin. Such constant chains are well known in the state of the art and e.g. described by Kabat, E. A., (see e.g. Johnson, G., Wu, T. T., Nucleic Acids Res. 28 (2000) 214-218). For example, a useful human heavy chain constant region comprises an amino acid sequence of SEQ ID NO: 25. For example, a useful human light chain constant region comprises an amino acid sequence of a kappa-light chain constant region of SEQ ID NO: 26. It is further preferred that the antibody is of mouse origin and comprises the antibody variable sequence frame of a mouse antibody according to Kabat.

Immunoconjugates

The invention also provides immunoconjugates comprising an anti-CSF-1R antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calichcamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med.

Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-malcimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Therapeutic Methods and Compositions

The invention comprises a method for the treatment of a patient in need of therapy, characterized by administering to the patient a therapeutically effective amount of an antibody according to the invention.

The invention comprises the use of an antibody according to the invention for therapy.

One preferred embodiment of the invention are the CSF-1R antibodies of the present invention for use in the treatment of "CSF-1R mediated diseases" or the CSF-1R antibodies of the present invention for use for the manufacture of a medicament in the treatment of "CSF-1R mediated diseases", which can be described as follows:

There are 3 distinct mechanisms by which CSF-1R signaling is likely involved in tumor growth and metastasis. The first is that expression of CSF-ligand and receptor has been found in tumor cells originating in the female reproductive system (breast, ovarian, endometrium, cervical) (Scholl, S. M., et al., J. Natl. Cancer Inst. 86 (1994) 120-126; Kacinski, B. M., Mol. Reprod. Dev. 46 (1997) 71-74; Ngan, H. Y., et al., Eur. J. Cancer 35 (1999) 1546-1550; Kirma, N., et al., Cancer Res 67 (2007) 1918-1926) and the expression has been associated with breast cancer xenograft growth as well as poor prognosis in breast cancer patients.

Two point mutations were seen in CSF-1R in about 10-20% of acute myelocytic leukemia, chronic myelocytic leukemia and myelodysplasia patients tested in one study, and one of mutations was found to disrupt receptor turnover (Ridge, S. A., et al., Proc. Natl. Acad. Sci USA 87 (1990) 1377-1380). However the incidence of the mutations could not be confirmed in later studies (Abu-Duhier, F. M., et al., Br. J. Haematol. 120 (2003) 464-470). Mutations were also found in some cases of hepatocellular cancer (Yang, D. H., et al., Hepatobiliary Pancreat. Dis. Int. 3 (2004) 86-89) and idiopathic myelofibrosis (Abu-Duhier, F., M., et al., Br. J. Haematol. 120 (2003) 464-470).

Pigmented villonodular synovitis (PVNS) and Tenosynovial Giant cell tumors (TGCT) can occur as a result of a translocation that fuses the M-CSF gene to a collagen gene COL6A3 and results in overexpression of M-CSF (West, R. B., et al., Proc. Natl. Acad. Sci. USA 103 (2006) 690-695). A landscape effect is proposed to be responsible for the resulting tumor mass that consists of monocytic cells attracted by cells that express M-CSF. TGCTs are smaller tumors that can be relatively easily removed from fingers where they mostly occur. PVNS is more aggressive as it can recur in large joints and is not as easily controlled surgically.

The second mechanism is based on blocking signaling through M-CSF/CSF-1R at metastatic sites in bone which induces osteoclastogenesis, bone resorption and osteolytic bone lesions. Breast, multiple myeloma and lung cancers are examples of cancers that have been found to metastasize to the bone and cause osteolytic bone disease resulting in skeletal complications. M-CSF released by tumor cells and stroma induces the differentiation of hematopoietic myeloid monocyte progenitors to mature osteoclasts in collaboration with the receptor activator of nuclear factor kappa-B ligand-RANKL. During this process, M-CSF acts as a permissive factor by giving the survival signal to osteoclasts (Tanaka, S., et al., J. Clin. Invest. 91 (1993) 257-263). Inhibition of CSF-1R activity during osteoclast differentiation and maturation with a anti-CSF-1R antibody is likely to prevent unbalanced activity of osteoclasts that cause osteolytic disease and the associated skeletal related events in metastatic disease. Whereas breast, lung cancer and multiple myeloma typically result in osteolytic lesions, metastasis to the bone in prostate cancer initially has an osteoblastic appearance in which increased bone forming activity results in 'woven bone' which is different from typical lamellar structure of normal bone. During disease progression bone lesions display a significant osteolytic component as well as high serum levels of bone resorption and suggests that anti-resorptive therapy may be useful. Bisphosphonates have been shown to inhibit the formation of osteolytic lesions and reduced the number of skeletal-related events only in men with hormone-refractory metastatic prostate cancer but at this point their effect on osteoblastic lesions is controversial and bisphosphonates have not been beneficial in preventing bone metastasis or hormone responsive prostate cancer to date. The effect of anti-resorptive agents in mixed osteolytic/ osteoblastic prostate cancer is still being studied in the clinic (Choueiri, M. B., et al., Cancer Metastasis Rev. 25 (2006) 601-609; Vessella, R. L. and Corey, E., Clin. Cancer Res. 12 (20 Pt 2) (2006) 6285s-6290s).

The third mechanism is based on the recent observation that tumor associated macrophages (TAM) found in solid tumors of the breast, prostate, ovarian and cervical cancers correlated with poor prognosis (Bingle, L., et al., J. Pathol. 196 (2002) 254-265; Pollard, J. W., Nat. Rev. Cancer 4 (2004) 71-78). Macrophages are recruited to the tumor by M-CSF and other chemokines. The macrophages can then contribute to tumor progression through the secretion of angiogenic factors, proteases and other growth factors and cytokines and may be blocked by inhibition of CSF-1R signaling. Recently it was shown by Zins, K., et al., Cancer Res. 67 (2007) 1038-1045) that expression of siRNA of Tumor necrosis factor alpha (TNF alpha), M-CSF or the combination of both would reduce tumor growth in a mouse xenograft model between 34% and 50% after intratumoral injection of the respective siRNA. SiRNA targeting the TNF alpha secreted by the human SW620 cells reduced mouse M-CSF levels and led to reduction of macrophages in the tumor. In addition treatment of MCF7 tumor xenografts with an antigen binding fragment directed against M-CSF did result in 40% tumor growth inhibition, reversed the resistance to chemotherapeutics and improved survival of the mice when given in combination with chemotherapeutics (Paulus, P., et al., Cancer Res. 66 (2006) 4349-4356).

TAMs are only one example of an emerging link between chronic inflammation and cancer. There is additional evidence for a link between inflammation and cancer as many chronic diseases are associated with an increased risk of cancer, cancers arise at sites of chronic inflammation, chemical mediators of inflammation are found in many cancers; deletion of the cellular or chemical mediators of inflammation inhibits development of experimental cancers and long-term use of anti-inflammatory agents reduce the risk of some cancers. A link to cancer exists for a number of inflammatory conditions among-those H. pylori induced gastritis for gastric cancer, Schistosomiasis for bladder cancer, HHIVX for Kaposi's sarcoma, endometriosis for ovarian cancer and prostatitis for prostate cancer (Balkwill, F., et al., Cancer Cell 7 (2005) 211-217). Macrophages are key cells in chronic inflammation and respond differentially to their microenvironment. There are two types of macrophages that are considered extremes in a continuum of functional states: M macrophages are involved in Type 1 reactions. These reactions involve the activation by microbial products and consequent killing of pathogenic microorganisms that result in reactive oxygen intermediates. On the other end of the extreme are M2 macrophages involved in Type 2 reactions that promote cell proliferation, tune inflammation and adaptive immunity and promote tissue remodeling, angiogenesis and repair (Mantovani, A., et al., Trends Immunol. 25 (2004) 677-686). Chronic inflammation resulting in established neoplasia is usually associated with M2 macrophages. A pivotal cytokine that mediates inflammatory reactions is TNF alpha that true to its name can stimulate anti-tumor immunity and hemorrhagic necrosis at high doses but has also recently been found to be expressed by tumor cells and acting as a tumor promoter (Zins, K., et al., Cancer Res. 67 (2007) 1038-1045; Balkwill, F., Cancer Metastasis Rev. 25 (2006) 409-416). The specific role of macrophages with respect to the tumor still needs to be better understood including the potential spatial and temporal dependence on their function and the relevance to specific tumor types.

Thus one embodiment of the invention are the CSF-1R antibodies of the present invention for use in the treatment of cancer. The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, ovarian cancer, cervical cancer, lung cancer or prostate cancer.

Preferably such cancers are further characterized by CSF-1 or CSF-1R expression or overexpression. One further embodiment the invention are the CSF-1R antibodies of the present invention for use in the simultaneous treatment of primary tumors and new metastases.

Thus another embodiment of the invention are the CSF-1R antibodies of the present invention for use in the treatment of periodontitis, histiocytosis X, osteoporosis, Paget's disease of bone (PDB), bone loss due to cancer therapy, periprosthetic osteolysis, glucocorticoid-induced osteoporosis, rheumatoid arthritis, psiratic arthritis, osteoarthritis, inflammatory arthridities, and inflammation. Rabello, D., et al., Biochem. Biophys. Res. Commun. 347 (2006) 791-796 has demonstrated that SNPs in the CSF1 gene exhibited a positive association with aggressive periodontitis: an inflammatory disease of the periodontal tissues that causes tooth loss due to resorption of the alveolar bone.

Histiocytosis X (also called Langerhans cell histiocytosis, LCH) is a proliferative disease of Langerhans dendritic cells that appear to differentiate into osteoclasts in bone and extraosseous LCH lesions. Langerhans cells are derived from circulating monocytes. Increased levels of M-CSF that have been measured in sera and lesions where found to correlate with disease severity (da Costa, C. E., et al., J. Exp. Med. 201 (2005) 687-693). The disease occurs primarily in a pediatric patient population and has to be treated with chemotherapy when the disease becomes systemic or is recurrent.

The pathophysiology of osteoporosis is mediated by loss of bone forming osteoblasts and increased osteoclast dependent bone resorption. Supporting data has been described by Cenci et al showing that an anti-M-CSF antibody injection preserves bone density and inhibits bone resorption in ovariectomized mice (Cenci, S., et al., J. Clin. Invest. 105 (2000) 1279-1287). Recently a potential link between postmenopausal bone loss due to estrogen deficiency was identified and found that the presence of TNF alpha producing T-cell affected bone metabolism (Roggia, C., et al., Minerva Med. 95 (2004) 125-132). A possible mechanism could be the induction of M-CSF by TNF alpha in vivo. An important role for M-CSF in TNF-alpha-induced osteoclastogenesis was confirmed by the effect of an antibody directed against M-CSF that blocked the TNF alpha induced osteolysis in mice and thereby making inhibitors of CSF-1R signaling potential targets for inflammatory arthritis (Kitaura, H., et al., J. Clin. Invest. 115 (2005) 3418-3427).

Paget's disease of bone (PDB) is the second most common bone metabolism disorder after osteoporosis in which focal abnormalities of increased bone turnover lead to complications such as bone pain, deformity, pathological fractures and deafness. Mutations in four genes have been identified that regulate normal osteoclast function and predispose individuals to PDB and related disorders: insertion mutations in TNFRSF11A, which encodes receptor activator of nuclear factor (NF) kappaB (RANK)-a critical regulator of osteoclast function, inactivating mutations of TNFRSF11B which encodes osteoprotegerin (a decoy receptor for RANK ligand), mutations of the sequestosome 1 gene (SQSTM1), which encodes an important scaffold protein in the NFkappaB pathway and mutations in the valosin-containing protein (VCP) gene. This gene encodes VCP, which has a role in targeting the inhibitor of NFkappaB for degradation by the proteasome (Daroszewska, A., Ralston, S. H., Nat. Clin. Pract. Rheumatol. 2 (2006) 270-277). Targeted CSF-1R inhibitors provide an opportunity to block the deregulation of the RANKL signaling indirectly and add an additional treatment option to the currently used bisphosphonates.

Cancer therapy induced bone loss especially in breast and prostate cancer patients is an additional indication where a targeted CSF-1R inhibitor could prevent bone loss (Lester, J. E., et al., Br. J. Cancer 94 (2006) 30-35). With the improved prognosis for early breast cancer the long-term consequences of the adjuvant therapies become more important as some of the therapies including chemotherapy, irradiation, aromatase inhibitors and ovary ablation affect bone metabolism by decreasing the bone mineral density, resulting in increased risk for osteoporosis and associated fractures (Lester, J. E., et al., Br. J. Cancer 94 (2006) 30-35). The equivalent to adjuvant aromatase inhibitor therapy in breast cancer is androgen ablation therapy in prostate cancer which leads to loss of bone mineral density and significantly increases the risk of osteoporosis-related fractures (Stoch, S. A., et al., J. Clin. Endocrinol. Metab. 86 (2001) 2787-2791).

Targeted inhibition of CSF-1R signaling is likely to be beneficial in other indications as well when targeted cell types include osteoclasts and macrophages e.g. treatment of specific complications in response to joint replacement as a consequence of rheumatoid arthritis. Implant failure due to periprosthetic bone loss and consequent loosing of prostheses is a major complication of joint replacement and requires repeated surgery with high socioeconomic burdens for the individual patient and the health-care system. To date, there is no approved drug therapy to prevent or inhibit periprosthetic ostolysis (Drees, P., et al., Nat. Clin. Pract. Rheumatol. 3 (2007) 165-171).

Glucocorticoid-induced osteoporosis (GIOP) is another indication in which a CSF-1R inhibitor could prevent bone loss after longterm glucocorticocosteroid use that is given as a result of various conditions among those chronic obstructive pulmonary disease, asthma and rheumatoid arthritis (Guzman-Clark, J. R., et al., Arthritis Rheum. 57 (2007) 140-146; Feldstein, A. C., et al., Osteoporos. Int. 16 (2005) 2168-2174).

Rheumatoid arthritis, psioratic arthritis and inflammatory arthridities are in itself potential indications for CSF-1R signaling inhibitors in that they consist of a macrophage component and to a varying degree bone destruction (Ritchlin, C. T., et al., J. Clin. Invest. 111 (2003) 821-831). Osteoarthritis and rheumatoid arthritis are inflammatory autoimmune disease caused by the accumulation of macrophages in the connective tissue and infiltration of macrophages into the synovial fluid, which is at least partially mediated by M-CSF. Campbell, I. K., et al., J. Leukoc. Biol. 68 (2000) 144-150, demonstrated that M-CSF is produced by human-joint tissue cells (chondrocytes, synovial fibroblasts) in vitro and is found in synovial fluid of patients with rheumatoid arthritis, suggesting that it contributes to the synovial tissue proliferation and macrophage infiltration which is associated with the pathogenesis of the disease. Inhibition of CSF-1R signaling is likely to control the number of macrophages in the joint and alleviate the pain from the associated bone destruction. In order to minimize adverse affects and to further understand the impact of CSF-1R signaling in these indications, one method is to specifically inhibit CSF-1R without targeting a myriad other kinases, such as Raf kinase.

Recent literature reports correlate increased circulating M-CSF with poor prognosis and atherosclerotic progression in chronic coronary artery disease (Saitoh, T., et al., J. Am. Coll. Cardiol. 35 (2000) 655-665; Ikonomidis, I., et al., Eur. Heart. J. 26 (2005) 1618-1624); M-CSF influences the atherosclerotic process by aiding the formation of foam cells (macrophages with ingested oxidized LDL) that express CSF-1R and represent the initial plaque (Murayama, T., et al., Circulation 99 (1999) 1740-1746).

Expression and signaling of M-CSF and CSF-1R is found in activated microglia. Microglia, which are resident macrophages of the central nervous system, can be activated by various insults, including infection and traumatic injury. M-CSF is considered a key regulator of inflammatory responses in the brain and M-CSF levels increase in HIV-1, encephalitis, Alzheimer's disease (AD) and brain tumors. Microgliosis as a consequence of autoerine signaling by M-CSF/CSF-1R results in induction of inflammatory cytokines and nitric oxides being released as demonstrated by e.g. using an experimental neuronal damage model (Hao, A. J., et al., Neuroscience 112 (2002) 889-900; Murphy, G. M., Jr., et al., J. Biol. Chem. 273 (1998) 20967-20971). Microglia that have increased expression of CSF-1R are found to surround plaques in AD and in the amyloid precursor protein V717F transgenic mouse model of AD (Murphy, G. M., Jr., et al., Am. J. Pathol. 157 (2000) 895-904). On the other hand op/op mice with fewer microglia in the brain resulted in fibrilar deposition of A-beta and neuronal loss compared to normal control suggesting that microglia do have a neuroprotective function in the development of AD lacking in the op/op mice (Kaku, M., et al., Brain Res. Brain Res. Protoc. 12 (2003) 104-108).

Expression and signaling of M-CSF and CSF-1R is associated with inflammatory bowel disease (IBD) (WO 2005/046657). The term "inflammatory bowel disease" refers to serious, chronic disorders of the intestinal tract characterised by chronic inflammation at various sites in the gastrointestinal tract, and specifically includes ulcerative colitis (UC) and Crohn's disease.

The invention the antibody characterized in comprising the antibody binding to human CSF-1R being characterized by the above mentioned epitope binding properties or alternatively by the above mentioned amino acid sequences and amino acid sequence fragments for the treatment of cancer.

The invention the antibody characterized in comprising the antibody binding to human CSF-1R being characterized by the above mentioned epitope binding properties or alternatively by the above mentioned amino acid sequences and amino acid sequence fragments for the treatment of bone loss.

The invention comprises the antibody characterized in comprising the antibody binding to human CSF-1R being characterized by the above mentioned epitope binding properties or alternatively by the above mentioned amino acid sequences and amino acid sequence fragments for the prevention or treatment of metastasis.

The invention comprises the antibody characterized in comprising the antibody binding to human CSF-1R being characterized by the above mentioned epitope binding properties or alternatively by the above mentioned amino acid sequences and amino acid sequence fragments for treatment of inflammatory diseases.

The invention comprises the use of an antibody characterized in comprising the antibody binding to human CSF-1R being characterized by the above mentioned epitope binding properties or alternatively by the above mentioned amino acid sequences and amino acid sequence fragments for the treatment of cancer or alternatively for the manufacture of a medicament for the treatment of cancer.

The invention comprises the use of an antibody characterized in comprising the antibody binding to human CSF-1R being characterized by the above mentioned epitope binding properties or alternatively by the above mentioned amino acid sequences and amino acid sequence fragments for the treatment of bone loss or alternatively for the manufacture of a medicament for the treatment of bone loss.

The invention comprises the use of an antibody characterized in comprising the antibody binding to human CSF-1R being characterized by the above mentioned epitope binding properties or alternatively by the above mentioned amino acid sequences and amino acid sequence fragments for the prevention or treatment of metastasis or alternatively for the manufacture of a medicament for the prevention or treatment of metastasis.

The invention comprises the use of an antibody characterized in comprising the antibody binding to human CSF-1R being characterized by the above mentioned epitope binding properties or alternatively by the above mentioned amino acid sequences and amino acid sequence fragments for treatment of inflammatory diseases or alternatively for the manufacture of a medicament for the treatment of inflammatory diseases. In one embodiment the antibodies according to the invention inhibit CSF-1 binding to CSF-1R with an IC50 of 75 ng/ml or lower, in one embodiment with an IC50 of 50 ng/ml or lower. The IC50 of inhibition of CSF-1 binding to CSF-1R can be determined as shown in Example 2.

In one embodiment the antibodies according to the invention inhibit CSF-1-induced CSF-1R phosphorylation (in NIH3T3-CSF-1R recombinant cells) with an IC50 of 150 ng/ml or lower, in one embodiment with an IC50 of 100 ng/ml or lower, in one embodiment with an IC50 of 50 ng/ml or lower, in one embodiment with an IC50 of 25 ng/ml or lower The IC50 of CSF-1-induced CSF-1R phosphorylation can be determined as shown in Example 3.

In one embodiment the antibodies according to the invention inhibit the growth of recombinant NIH3T3 cells expressing human CSF-1R (SEQ ID No: 15) by 80% or more (as compared to the absence of antibody), preferably by 90% or more. The % growth inhibition is determined as shown in Example 6 wherein the % survival is measured. From the % survival the % growth inhibition are calculated as follows: % growth inhibition=100–% survival. E.g. <CSF-1R>7G5.3B6 shows a growth inhibition of wt human CSF-1R expressing NIH3T3 cells of 100-2=98%.

In one embodiment the antibodies according to the invention stimulate the growth of recombinant NIH3T3 cells expressing human mutant CSF-1R L301S Y969F (SEQ ID No: 16) by 5% or more (as compared to the absence of antibody), in one embodiment by 20% or more. The % growth stimulation is determined as shown in Example 6 wherein the % survival is measured. From the % survival the % growth stimulation are calculated as follows: % growth stimulation=–(100–% survival). E.g. <CSF-1R>7G5.3B6 shows a growth stimulation of mutant human CSF-1R expressing NIH3T3 cells of –(100–0)=–(100–112) %=+12%.

In one embodiment the antibodies according to the invention inhibit the growth of BeWo tumor cells (ATCC CCL-98) by 70% or more (at a antibody concentration of 10 µg/ml; and as compared to the absence of antibody), preferably by 80% or more. The % growth inhibition is determined as shown in Example 7. E.g. <CSF-1R>7G5.3B6 shows a growth inhibition of BeWo tumor cells of 89%.

In one embodiment the antibodies according to the invention inhibit macrophage differentiation. In one embodiment the antibodies according to the invention inhibit the survival of monocytes with an IC50 of 1.5 nM or lower, preferably with an IC50 of 1.0 nM or lower. The inhibition of the survival of monocytes is determined as shown in Example 8.

A further embodiment of the invention is a method for the production of an antibody against CSF-1R characterized in that the sequence of a nucleic acid encoding the heavy chain of a human IgG1 class antibody binding to human CSF-1R according to the invention said modified nucleic acid and the nucleic acid encoding the light chain of said antibody are inserted into an expression vector, said vector is inserted in a eukaryotic host cell, the encoded protein is expressed and recovered from the host cell or the supernant.

Pharmaceutical Formulations

The term "pharmaceutical formulation" refers to a preparation which is in such form as to permit the biological activity of an active ingredient contained therein to be effective, and which contains no additional components which are unacceptably toxic to a subject to which the formulation would be administered.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative. As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from cancer, especially from colon, lung or pancreas cancer.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from cancer.

The invention also provides the use of an antibody according to the invention in an effective amount for the manufacture of a pharmaceutical agent, preferably together with a pharmaceutically acceptable carrier, for the treatment of a patient suffering from cancer.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-CSF-1R antibody.

The following examples and sequence listing are provided to aid the understanding of the present invention, the true scope of which is set forth in the appended claims. It is understood that modifications can be made in the procedures set forth without departing from the spirit of the invention.

Antibody Deposition

| Cell line | Deposition No. | Date of Deposit |
|---|---|---|
| <CSF-1R->7H5.2G10 | DSM ACC2922 | Oct. 6, 2008 |

Description of the Sequences

SEQ ID NO: 1 heavy chain CDR3, <CSF-1R>7H5.2G10
SEQ ID NO: 2 heavy chain CDR2, <CSF-1R>7H5.2G10
SEQ ID NO: 3 heavy chain CDR1, <CSF-1R>7H5.2G10
SEQ ID NO: 4 light chain CDR3, <CSF-1R>7H5.2G10
SEQ ID NO: 5 light chain CDR2, <CSF-1R>7H5.2G10
SEQ ID NO: 6 light chain CDR1, <CSF-1R>7H5.2G10
SEQ ID NO: 7 heavy chain variable domain, <CSF-1R>7H5.2G10
SEQ ID NO: 8 light chain variable domain, <CSF-1R>7H5.2G10
SEQ ID NO: 9 heavy chain CDR3, <CSF-1R>10A4.1G11
SEQ ID NO: 10 heavy chain CDR2, <CSF-1R>10A4.1G11
SEQ ID NO: 11 heavy chain CDR1, <CSF-1R>10A4.1G11
SEQ ID NO: 12 light chain CDR3, <CSF-1R>10A4.1G11
SEQ ID NO: 13 light chain CDR2, <CSF-1R>10A4.1G11
SEQ ID NO: 14 light chain CDR1, <CSF-1R>10A4.1G11
SEQ ID NO: 15 heavy chain variable domain, <CSF-1R>10A4.1G11
SEQ ID NO: 16 light chain variable domain, <CSF-1R>10A4.1G11
SEQ ID NO: 17 heavy chain CDR3, <CSF-1R>6G4.1C8
SEQ ID NO: 18 heavy chain CDR2, <CSF-1R>6G4.1C8
SEQ ID NO: 19 heavy chain CDR1, <CSF-1R>6G4.1C8
SEQ ID NO: 20 light chain CDR3, <CSF-1R>6G4.1C8
SEQ ID NO: 21 light chain CDR2, <CSF-1R>6G4.1C8
SEQ ID NO: 22 light chain CDR1, <CSF-1R>6G4.1C8
SEQ ID NO: 23 heavy chain variable domain, <CSF-1R>6G4.1C8

SEQ ID NO: 24 light chain variable domain, <CSF-1R>6G4.1C8
SEQ ID NO: 25 gamma1 heavy chain constant region
SEQ ID NO: 26 κ light chain constant region
SEQ ID NO: 27 human heavy chain constant region derived from IgG1
SEQ ID NO: 28 human heavy chain constant region derived from IgG1 mutated on L234A and L235A
SEQ ID NO: 29 human heavy chain constant region derived from IgG4
SEQ ID NO: 30 human heavy chain constant region derived from IgG4 mutated onS228P
SEQ ID NO: 31 wildtype CSF-1R (wt CSF-1R)
SEQ ID NO: 32 mutant CSF-1R L301S Y969F The following examples, sequence listing and figures are provided to aid the understanding of the present invention, the true scope of which is set forth in the appended claims. It is understood that modifications can be made in the procedures set forth without departing from the spirit of the invention.

III. Examples

EXAMPLE 1

Generation of a Hybridoma Cell Line Producing Anti-CSF-1R Antibodies

Immunization Procedure of NMRI Mice

NMRI mice were immunized with an expression vector pDisplay™ (Invitrogen, USA) encoding the extracellular domain of huCSF-1R by utilizing electroporation. Every mouse was 4 times immunized with 100 μg DNA. When serum titers of anti-huCSF-1R were found to be sufficient, mice were additionally boosted once with 50 μg of a 1:1 mixture huCSF-1R ECD/huCSF-1R ECDhuFc chimera in 200 μl PBS intravenously (i.v.) 4 and 3 days before fusion.

Antigen Specific ELISA

Anti-CSF-1R titers in sera of immunized mice were determined by antigen specific ELISA.

0.3 μg/ml huCSF-1R-huFc chimera (soluble extracellular domain) was captured on a streptavidin plate (MaxiSorb; MicroCoat, DE, Cat. No. 11974998/MC1099) with 0.1 mg/ml biotinylated anti Fcγ (Jackson ImmunoResearch., Cat. No. 109-066-098) and horse radish peroxidase (HRP)-conjugated F(ab')₂ anti mouse IgG (GE Healthcare, UK, Cat. No. NA9310V) diluted 1/800 in PBS/0.05% Tween20/0.5% BSA was added. Sera from all taps were diluted 1/40 in PBS/0.05% Tween20/0.5% BSA and serially diluted up to 1/1638400. Diluted sera were added to the wells. Pre-tap serum was used as negative control. A dilution series of mouse anti-human CSF-1R Mab3291 (R&D Systems, UK) from 500 ng/ml to 0.25 ng/ml was used as positive control. All components were incubated together for 1.5 hours, Wells were washed 6 times with PBST (PBS/0.2% Tween20) and assays were developed with freshly prepared ABTS™ solution (1 mg/ml) (ABTS: 2,2'-azino bis(3-ethylbenzthiazoline-6-sulfonic acid) for 10 minutes at RT. Absorbance was measured at 405 nm.

Hybridoma Generation

The mouse lymphocytes can be isolated and fused with a mouse myeloma cell line using PEG based standard protocols to generate hybridomas. The resulting hybridomas are then screened for the production of antigen-specific antibodies. For example, single cell suspensions of splenic derived lymphocytes from immunized mice are fused to Ag8 non-secreting mouse myeloma cells P3X63Ag8.653 (ATCC, CRL-1580) with 50% PEG. Cells are plated at approximately $10^4$ in flat bottom 96 well micro titer plate, followed by about two weeks incubation in selective medium. Individual wells are then screened by ELISA for human anti-CSF-1R monoclonal IgM and IgG antibodies. Once extensive hybridoma growth occurs, the antibody secreting hybridomas are replated, screened again, and if still positive for human IgG, anti-CSF-1R monoclonal antibodies, can be subcloned by FACS. The stable subclones are then cultured in vitro to produce antibody in tissue culture medium for characterization.

Culture of Hybridomas

Generated muMAb hybridomas were cultured in RPMI 1640 (PAN—Catalogue No. (Cat. No.) PO4-17500) supplemented with 2 mM L-glutamine (GIBCO—Cat. No. 35050-038), 1 mM Na-Pyruvat (GIBCO—Cat. No. 11360-039), ix NEAA (GIBCO—Cat. No. 11140-035), 10% FCS (PAA—Cat. No. A15-649), Ix Pen Strep (Roche—Cat. No. 1074440), 1× Nutridoma CS (Roche—Cat. No. 1363743), 50 μM Mercaptoethanol (GIBCO—Cat. No. 31350-010) and 50 U/ml IL 6 mouse (Roche—Cat. No. 1 444 581) at 37° C. and 5% $CO_2$.

EXAMPLE 2

Inhibition of CSF-1 Binding to CSF-1R (ELISA)

The test was performed on 384 well microtiter plates (MicroCoat. DE. Cat. No. 464718) at RT. After each incubation step plates were washed 3 times with PBST.

At the beginning, plates were coated with 0.5 mg/ml goat F(ab')₂ biotinylated anti Fcγ (Jackson ImmunoResearch., Cat. No. 109-006-170) for 1 hour (h).

Thereafter the wells were blocked with PBS supplemented with 0.2% Tween®-20 and 2% BSA (Roche Diagnostics GmbH, DE) for 0.5 h. 75 ng/ml of huCSF-1R-huFc chimera (soluble extracellular domain) was immobilized to plate for 1 h. Then dilutions of purified antibodies in PBS/0.05% Tween20/0.5% BSA were incubated for 1 h. After adding a mixture of 3 ng/ml CSF-1 (Biomol, DE, Cat. No. 60530), 50 ng/ml biotinylated anti CSF-1 clone BAF216 (R&D Systems, UK) and 1:5000 diluted streptavidin HRP (Roche Diagnostics GmbH, DE, Cat. No. 11089153001) for 1 h the plates were washed 6 times with PBST. Anti CSF-1R SC-02, clone 2-4A5 (Santa Cruz Biotechnology, US), which inhibits the ligand-receptor interaction, was used as positive control. Plates were developed with freshly prepared BM Blue® POD substrate solution (BM Blue®: 3,3'-5,5'-Tetramethylbenzidine, Roche Diagnostics GmbH, DE, Cat. No. 11484281001) for 30 minutes at RT. Absorbance was measured at 370 nm. All anti-CSF-1R antibodies showed significant inhibition of the CSF-1 binding to CSF-1R (see Table 1). Anti CSF-1R SC-02, clone 2-4A5 (Santa Cruz Biotechnology, US), which inhibits the ligand-receptor interaction, was used as reference control.

TABLE 1

Calculated IC50 values for the inhibition of the CSF-1/CSF-1R interaction

| Antibody | IC50 CSF-1/CSF-1R Inhibition [ng/ml] |
|---|---|
| <CSF-1R>7H5.2G10 | 26.9 |
| <CSF-1R>10A4.1G11 | 63.4 |
| <CSF-1R>6G4.1C8 | 21.2 |
| SC-02, clone 2-4A5 | 30.9 |

EXAMPLE 3

Inhibition of CSF-1-Induced CSF-1R Phosphorylation in NIH3T3-CSF-1R Recombinant Cells 4.5×10³ NIH 3T3 cells, retrovirally infected with an expression vector for full-length CSF-1R, were cultured in DMEM (PAA Cat. No. E15-011), 2 mM L-glutamine (Sigma, Cat. No. G7513, 2 mM Sodium pyruvate, 1× nonessential aminoacids, 10% FKS (PAA, Cat. No. A15-649) and 100 µg/ml PenStrep (Sigma, Cat. No. P4333 [10 mg/ml]) until they reached confluency. Thereafter cells were washed with serum-free DMEM media (PAA Cat. No. E5-011) supplemented with sodium selenite [5 ng/ml] (Sigma, Cat. No. S9133), transferrin [10 µg/ml] (Sigma, Cat. No. T8158), BSA [400 µg/ml] (Roche Diagnostics GmbH, Cat. No. 10735078), 4 mM L-glutamine (Sigma, Cat. No. G7513), 2 mM sodium pyruvate (Gibco, Cat. No. 11360), 1× nonessential aminoacids (Gibco, Cat: 11140-035), 2-mercaptoethanol [0.05 mM] (Merck, Cat. No. M7522), 100 µg/ml and PenStrep (Sigma, Cat. No. P4333) and incubated in 30 µl of the same medium for 16 hours to allow for receptor up-regulation. 10 µl of diluted anti-CSR-1R antibodies were added to the cells for 1.5 h. Then cells were stimulated with 10 µl of 100 ng/ml huM-CSF-1 (Biomol Cat. No. 60530) for 5 min. After the incubation, supernatant was removed, cells were washed twice with 80 µl of ice-cold PBS and 50 µl of freshly prepared ice-cold lysis buffer (150 mM NaCl/20 mM Tris pH 7.5/1 mM EDTA/1 mM EGTA/1% Triton X-100/1 protease inhibitor tablet (Roche Diagnostics GmbH Cat. No. 1 836 170) per 10 ml buffer/10 µl/ml phosphatase inhibitor cocktail 1 (Sigma Cat. No. P-2850, 100× Stock)/10 µl/ml protcase inhibitor 1 (Sigma Cat. No. P-5726, 100× Stock)/10 µl/ml 1 M NaF) was added. After 30 minutes on ice the plates were shaken vigourously on a plateshaker for 3 minutes and then centrifuged 10 minutes at 2200 rpm (Heraeus Megafuge 10).

The presence of phosphorylated and total CSF-1 receptor in the cell lysate was analyzed with Elisa. For detection of the phosphorylated receptor the kit from R&D Systems (Cat. No. DYC3268-2) was used according to the instructions of the supplier. For detection of total CSF-1R 10 µl of the lysate was immobilized on plate by use of the capture antibody contained in the kit. Thereafter 1:750 diluted biotinylated anti CSF-1R antibody BAF329 (R&D Systems) and 1:1000 diluted streptavidin-HRP conjugate was added. After 60 minutes plates were developed with freshly prepared ABTS® solution and the absorbance was detected. Data were calculated as % of positive control without antibody and the ratio value phospho/total receptor expressed. The negative control was defined without addition of M-CSF-1. Anti CSF-1R SC-02, clone 2-4A5 (Santa Cruz Biotechnology, US, see also Sherr, C. J., et al., Cell 41 (1985) 665-676), which inhibits the ligand-receptor interaction, was used as reference control.

TABLE 2

Calculated $IC_{50}$ values for the inhibition of CSF-1 receptor phosphorylation.

| Antibody | IC50 CSF-1R Phosphorylation [ng/ml] |
|---|---|
| <CSF-1R>7H5.2G10 | 49.0 |
| <CSF-1R>10A4.1G11 | 15.4 |
| <CSF-1R>6G4.1C8 | 82.6 |
| SC-02, clone 2-4A5 | 412.0 |

EXAMPLE 4

Determination of the Affinity of Anti-CSF-1R Antibodies to CSF-1R
Instrument: BIACORE® A 100
Chip: CM5 (Biacore BR-1006-68)
Coupling: amine coupling
Buffer: PBS (Biacore BR-1006-72), pH 7.4, 35° C.

For affinity measurements 36 µg/ml anti mouse Fcγ antibodies (from goat. Jackson Immuno Reasearch JIR115-005-071) have been coupled to the chip surface for capturing the antibodies against CSF-1R. CSF-1R ECD (R&D-Systems 329-MR or in-house subcloned pCMV-presS-HisAvitag-hCSF-1R-ECD were added in various concentrations in solution. Association was measured by an CSF-1R-injection of 1.5 minutes at 35° C.; dissociation was measured by washing the chip surface with buffer for 10 minutes at 35° C. Anti CSF-1R SC-02, clone 2-4A5 (Santa Cruz Biotechnology, US: see also Sherr, C. J., et al., Cell 41 (1985) 665-676), which inhibits the ligand-receptor interaction, was used as reference control.

For calculation of kinetic parameters the Langmuir 1:1 model was used.

TABLE 3

Affinity data measured by SPR (BIACORE ® A100) at 35° C.

| Antibody | $K_D$ (nM) | $k_a$ (1/Ms) | $k_d$ (1/s) | $t_{1/2}$ (mm) |
|---|---|---|---|---|
| <CSF-1R>7H5.2G10 | 0.54 | 7.0E±05 | 3.8E−04 | 30.40 |
| <CSF-1R>10A4.1G11 | 1.77 | 7.4E±05 | 1.3E−03 | 8.89 |
| <CSF-1R>6G4.1C8 | 0.52 | 5.7E±05 | 2.9E−04 | 39.43 |
| SC-02, clone 2-4A5 | 2.73 | 5.09E±05 | 1.39E−03 | 8.31 |

EXAMPLE 5

Epitope Mapping of Anti-CSF-1R Monoclonal Antibodies Based on Cross-Competition by Utilizing SPR
Instrument: BIACORE® A100
Chip: CM5 (Biacore BR-1006-68)
Coupling: amine coupling
Buffer: PBS (Biacore BR-1006-72), pH 7.4, 25° C.

For epitope mapping assays via cross-competition 36 µg/ml anti mouse Fcγ antibodies or anti rat Fcγ antibodies (from goat, Jackson Immuno Research Cat. No. 115-005-071 and Cat. No. 112-005-071) have been coupled to sensor chip surface for presentation of the antibody against CSF-1R. After capture from 5 µg/ml anti-CSF-1R monoclonal antibodies free binding capacities of capture antibodies have been blocked with 250 µg/ml mouse or rat immunoglobulins (Pierce Cat. No. 31202 and Pierce Cat. No. 31233), followed by injection of 12.5 µg/ml CSF-1R (R&D-Systems Cat. No. 329-MR) for 2 min. Binding of second anti-CSF-1R antibody has been analyzed by injection for 2 min, dissociation was measured by washing with buffer for 5 minutes. The assay and the measurements were conducted at 25° C. The specific binding of the second anti-CSF-1R antibody has been referenced against spot with the same chip setup up but only without injection of CSF-1R. The cross competition data have been calculated in percentage (%) of expected binding response of the second anti-CSF-1R antibody. The item "percentage (%) of expected binding response" for binding of the second antibody was calculated by "100*relativeResponse(general_stability_early)/rMax", where rMax is calculated by "relativeResponse(general_stability_late) *antibody molecular weight/antigen molecular weight" as described in Biacore epitope mapping instruction (for BIACORE® A100 instrument).s.

The minimal binding response was also calculated from the pairs of identical antibody 1 and 2. Thereof the obtained maximal value+50% was set as threshold for significant binding competition (see table X e.g. for antibody <CSF-1R>7H5.2G10 calculated threshold is 7+3.5=10.5). Thus an "anti-CSF-1R antibody binding to the same epitope as <CSF-1R>7H5.2G10" has a percentage (%) of expected binding response >10.5.

The anti-CSF-1R SC-02, clone 2-4A5 (Santa Cruz Biotechnology, US, see also Sherr, C. J., et al., Cell 41 (1985) 665-676), which inhibit the ligand-receptor interaction, was used as reference control.

TABLE 4

The epitope mapping via cross-competition data of anti CSF-1R antibodies

| | Antibody 2 | | |
|---|---|---|---|
| Antibody 1 | <CSF-1R> 7H5.2G10 | <CSF-1R> 10A4.1G11 | SC-02, clone 2-4A5 |
| <CSF-1R> 7H5.2G10 | 7 | 3 | 42 |
| <CSF-1R> 10A4.1G11 | 5 | −3 | 24 |
| SC-02, clone 2-4A5 | 51 | 39 | −2 |

The results indicate that the antibodies <CSF-1R>7H5.2G10, <CSF-1R>10A4.1G111, all bind to the same epitope, while e.g. SC-2-4A5 binds to another epitope and does not crossreact (crosscompete for binding) with the antibodies according to the invention.

EXAMPLE 6

Growth Inhibition of NIH3T3-CSF-1R Recombinant Cells in 3D Culture Under Treatment with Anti-CSF-1R Monoclonal Antibodies (CellTiterGlo-Assay)

NIH 3T3 cells, retrovirally infected with either an expression vector for full-length wildtype CSF-1R (SEQ ID No: 31) or mutant CSF-1R L301S Y969F (SEQ ID No: 32), were cultured in DMEM high glucose media (PAA, Pasching, Austria) supplemented with 2 mM L-glutamine, 2 mM sodium pyruvate and non-essential amino acids and 10% fetal bovine serum (Sigma, Taufkirchen, Germany) on poly-HEMA (poly(2-hydroxyethylmethacrylate)) (Polysciences, Warrington, Pa., USA)) coated dishes to prevent adherence to the plastic surface. Cells are seeded in medium replacing serum with 5 ng/ml sodium selenite, 10 mg/ml transferrin, 400 µg/ml BSA and 0.05 mM 2-mercaptoethanol. When treated with 100 ng/ml huCSF-1 (Biomol, Hamburg, Germany) wtCSF-1R expressing cells form dense spheroids that grow three dimensionally, a property that is called anchorage independence. These spheroids resemble closely the three dimensional architecture and organization of solid tumors in situ. Mutant CSF-1R recombinant cells are able to form spheroids independent of the CSF-1 ligand. Spheroid cultures were incubated for 3 days in the presence of 10 µg/ml antibody. The CellTiterGlo assay was used to detect cell viability by measuring the ATP-content of the cells.

TABLE 5

| Antibody | NIH3T Cells expressing wtCSF-1R % survival | NIH3T Cells expressing Mutant CSF-1R % survival |
|---|---|---|
| <CSF-1R>7H5.2G10 | 2 | 112 |
| <CSF-1R>10A4.1G11 | 3 | 144 |
| <CSF-1R>6G4.1C8 | 3 | 91 |
| SC-02, clone 2-4A5 | 62** | 66*** |

**average of 15 different experiments,
***average of 6 different experiments

EXAMPLE 7

Growth Inhibition of BeWo Tumor Cells in 3D Culture Under Treatment with Anti-CSF-1R Monoclonal Antibodies (CellTiterGlo-Assay)

BeWo choriocarcinoma cells (ATCC CCL-98) were cultured in F12K media (Sigma, Steinheim, Germany) supplemented with 10% FBS (Sigma) and 2 mM L-glutamine. $5 \times 10^4$ cells/well were seeded in 96-well poly-HEMA (poly (2-hydroxyethylmethacrylate)) coated plates containing F12K medium supplemented with 0.5% FBS and 5% BSA. Concomitantly, 200 ng/ml huCSF-1 and 10 µg/ml of different anti-CSF-1R monoclonal antibodies were added and incubated for 6 days. The CellTiterGlo assay was used to detect cell viability by measuring the ATP-content of the cells in relative light units (RLU). When BeWo spheroid cultures were treated with different anti-CSF-1R antibodies (10 µg/ml) inhibition of CSF-1 induced growth was observed. To calculate antibody-mediated inhibition the mean RLU value of unstimulated BeWo cells was subtracted from all samples. Mean RLU value of CSF-1 stimulated cells was set arbitrarily to 100%. Mean RLU values of cells stimulated with CSF-1 and treated with anti-CSF-1R antibodies were calculated in % of CSF-1 stimulated RLUs. The Table 6 shows the calculated data; FIG. 1 depicts mean RLU values. Each mean value was derived from triplicates.

TABLE 6

| Antibody | % inhibition 10 µg/ml antibody concentration |
|---|---|
| CSF-1 only | 0 |
| <CSF-1R>7H5.2G10 | 89 |
| <CSF-1R>10A4.1G11 | 83 |
| SC-02, clone 2-4A5 | 40 |

EXAMPLE 8

Inhibition of Macrophage Differentiation/Monocyte Survival Under Treatment with Anti-CSF-1R Monoclonal Antibodies (CellTiterGlo-Assay)

Monocytes isolated from peripheral blood using the RosetteSep™ Human Monocyte Enrichment Cocktail (StemCell Tech.—Cat. No. 15028). Enriched monocyte populations were seeded into 96 well microtiterplates ($2.5 \times 10^4$ cells/well) in 100 µl RPMI 1640 (Gibco—Cat. No. 31870) supplemented with 10 FCS (GIBCO—Cat. No. 011-090014M), 4 mM L-glutamine (GIBCO—Cat. No. 25030) and Ix PenStrep (Roche Cat. No. 1 074 440) at 37° C. and 5% $CO_2$. When 150 ng/ml huCSF-1 was added to the medium, a clear differentiation into adherent macrophages could be observed. This differentiation could be inhibited by addition of anti-CSF-1R antibodies. Concomitantly, the monocyte survival is affected and could be analyzed by CellTiterGlo (CTG) analysis. From the concentration dependent inhibition of the survival of monocytes by antibody treatment an $IC_{50}$ was calculated (see Table 7).

TABLE 7

| Antibody | $IC_{50}$ [nM] |
|---|---|
| <CSF-1R>7H.5.2G10 | 1.0 |
| <CSF-1R>10A4.1G11 | 0.4 |
| SC-02, clone 2-4A5 | 2.4 |

The invention claimed is:

1. An antibody that binds to human CSF-1R, wherein the antibody comprises a heavy chain variable domain comprising a CDR3 region of SEQ ID NO: 9, a CDR2 region of SEQ ID NO: 10, and a CDR1 region of SEQ ID NO:11, and a light chain variable domain comprising a CDR3 region of SEQ ID NO 12, a CDR2 region of SEQ ID NO:13, and a CDR1 region of SEQ ID NO:14.

2. The antibody according to claim 1, wherein the antibody comprises a heavy chain variable domain comprising the amino acid sequence of SEQ ID NO: 15, and a light chain variable domain comprising the amino acid sequence of SEQ ID NO:16.

3. The antibody according to claim 1, wherein the antibody is an antibody fragment that binds to human CSF-1R.

4. The antibody according to claim 1, wherein the antibody is of a human IgG4 subclass or a human IgG1 subclass antibody, or antibody fragment thereof.

5. The antibody according to claim 1, wherein the antibody is a monoclonal antibody.

6. The antibody according to claim 1, wherein the antibody is a CDR grafted, humanized, T cell epitope depleted, chimeric, single chain, or multispecific antibody.

7. An immunoconjugate comprising the antibody of claim 1 and a cytotoxic agent.

8. The immunoconjugate according to claim 7, wherein the cytotoxic agent is a chemotherapeutic agent, a growth inhibitory agent, a toxin, or a radioactive isotope.

9. A pharmaceutical composition comprising the antibody, or antibody fragment thereof, of claim 1.

10. The pharmaceutical composition of claim 9, further comprising a pharmaceutically acceptable carrier.

11. The antibody of claim 1 for the treatment of cancer.

12. The antibody of claim 1 for the treatment of bone loss.

13. The antibody of claim 1 for the prevention or treatment of metastasis.

14. The antibody of claim 1 for the treatment of inflammatory diseases.

* * * * *

SEQUENCE LISTING

<160> NUMBER OF SEQ ID NOS: 32

<210> SEQ ID NO 1
<211> LENGTH: 13
<212> TYPE: PRT
<213> ORGANISM: Mus musculus

<400> SEQUENCE: 1

Gly Gly Gly Asp Phe Thr Thr Gly Tyr Thr Met Asp Tyr
1               5                   10

<210> SEQ ID NO 2
<211> LENGTH: 17
<212> TYPE: PRT
<213> ORGANISM: Mus musculus

<400> SEQUENCE: 2

Leu Ile Ile Pro Tyr Asn Gly Gly Thr Ser Tyr Asn His Asn Phe Arg
1               5                   10                  15

Gly

<210> SEQ ID NO 3
<211> LENGTH: 10
<212> TYPE: PRT
<213> ORGANISM: Mus musculus

<400> SEQUENCE: 3

Gly Tyr Ser Phe Thr Asp Tyr Thr Val Asn
1               5                   10

<210> SEQ ID NO 4
<211> LENGTH: 9
<212> TYPE: PRT
<213> ORGANISM: Mus musculus

<400> SEQUENCE: 4

Gln Gln Tyr Trp Ser Ile Pro Trp Thr
1               5

<210> SEQ ID NO 5
<211> LENGTH: 7
<212> TYPE: PRT
<213> ORGANISM: Mus musculus

<400> SEQUENCE: 5

Gly Ala Thr Ser Leu Glu Thr
1               5

<210> SEQ ID NO 6
<211> LENGTH: 11
<212> TYPE: PRT
<213> ORGANISM: Mus musculus

<400> SEQUENCE: 6

Lys Ala Ser Asp His Ile His Asp Trp Leu Ala
1               5                   10

<210> SEQ ID NO 7
<211> LENGTH: 122
<212> TYPE: PRT
<213> ORGANISM: Mus musculus

<400> SEQUENCE: 7

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
                20                  25                  30

Thr Val Asn Trp Val Lys Gln Ser His Gly Glu Asn Leu Asp Trp Ile
            35                  40                  45

Gly Leu Ile Ile Pro Tyr Asn Gly Gly Thr Ser Tyr Asn His Asn Phe
    50                  55                  60

Arg Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Thr Arg Gly Gly Gly Asp Phe Thr Thr Gly Tyr Thr Met Asp Tyr Trp
            100                 105                 110

Gly His Gly Thr Ser Val Thr Val Ser Ser
        115                 120

<210> SEQ ID NO 8
<211> LENGTH: 108
<212> TYPE: PRT
<213> ORGANISM: Mus musculus

<400> SEQUENCE: 8

Asp Ile Gln Met Thr Gln Ser Ser Tyr Leu Ser Val Ser Leu Gly
1               5                   10                  15

Gly Thr Val Thr Ile Asn Cys Lys Ala Ser Asp His Ile His Asp Trp
                20                  25                  30

Leu Ala Trp Tyr Gln Gln Pro Gly Asn Ala Pro Arg Leu Leu Ile
            35                  40                  45

Ser Gly Ala Thr Ser Leu Glu Thr Gly Val Pro Ser Arg Phe Ser Gly
    50                  55                  60

Gly Gly Ser Gly Lys Asp Tyr Ser Leu Ile Ile Thr Ser Leu Gln Thr
65                  70                  75                  80

Glu Asp Phe Ala Thr Tyr Tyr Cys Gln Gln Tyr Trp Ser Ile Pro Trp
                85                  90                  95

Thr Phe Gly Gly Gly Thr Lys Leu Glu Ile Lys Arg
            100                 105

<210> SEQ ID NO 9
<211> LENGTH: 8
<212> TYPE: PRT
<213> ORGANISM: Mus musculus

<400> SEQUENCE: 9

Trp Arg Phe Phe Ala Met Asp Tyr
1               5

<210> SEQ ID NO 10
<211> LENGTH: 17
<212> TYPE: PRT
<213> ORGANISM: Mus musculus

<400> SEQUENCE: 10

Asp Ile Asn Pro Asn Tyr Asp Ser Thr Thr Tyr Asn Gln Lys Phe Lys
1               5                   10                  15

Gly

```
<210> SEQ ID NO 11
<211> LENGTH: 9
<212> TYPE: PRT
<213> ORGANISM: Mus musculus

<400> SEQUENCE: 11

Tyr Thr Phe Thr Asp Tyr Asn Met Asp
1               5

<210> SEQ ID NO 12
<211> LENGTH: 9
<212> TYPE: PRT
<213> ORGANISM: Mus musculus

<400> SEQUENCE: 12

Gln Gln Tyr Trp Ser Ile Pro Trp Thr
1               5

<210> SEQ ID NO 13
<211> LENGTH: 9
<212> TYPE: PRT
<213> ORGANISM: Mus musculus

<400> SEQUENCE: 13

Ile Ser Gly Ala Ser Ser Leu Glu Thr
1               5

<210> SEQ ID NO 14
<211> LENGTH: 11
<212> TYPE: PRT
<213> ORGANISM: Mus musculus

<400> SEQUENCE: 14

Lys Ala Ser Glu Asp Ile Tyr Asn Arg Leu Ala
1               5                   10

<210> SEQ ID NO 15
<211> LENGTH: 117
<212> TYPE: PRT
<213> ORGANISM: Mus musculus

<400> SEQUENCE: 15

Glu Val Gln Leu Gln Gln Phe Gly Thr Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Tyr Asp Ser Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Trp Arg Phe Phe Ala Met Asp Tyr Trp Gly Gln Gly Thr Ser
            100                 105                 110

Val Thr Val Ser Ser
        115
```

<210> SEQ ID NO 16
<211> LENGTH: 108
<212> TYPE: PRT
<213> ORGANISM: Mus musculus

<400> SEQUENCE: 16

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Ser Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ile Pro Trp
                85                  90                  95

Thr Phe Gly Gly Gly Thr Lys Leu Glu Ile Lys Arg
            100                 105

<210> SEQ ID NO 17
<211> LENGTH: 13
<212> TYPE: PRT
<213> ORGANISM: Mus musculus

<400> SEQUENCE: 17

Gly Gly Gly Asp Phe Thr Thr Gly Tyr Thr Met Asp Tyr
1               5                   10

<210> SEQ ID NO 18
<211> LENGTH: 17
<212> TYPE: PRT
<213> ORGANISM: Mus musculus

<400> SEQUENCE: 18

Leu Ile Ile Pro Tyr Asn Gly Gly Thr Ser Tyr Asn His Asn Phe Arg
1               5                   10                  15

Gly

<210> SEQ ID NO 19
<211> LENGTH: 10
<212> TYPE: PRT
<213> ORGANISM: Mus musculus

<400> SEQUENCE: 19

Gly Tyr Ser Phe Thr Asp Tyr Thr Val Asn
1               5                   10

<210> SEQ ID NO 20
<211> LENGTH: 9
<212> TYPE: PRT
<213> ORGANISM: Mus musculus

<400> SEQUENCE: 20

Gln Gln Tyr Trp Ser Ile Pro Trp Thr
1               5

<210> SEQ ID NO 21
<211> LENGTH: 7
<212> TYPE: PRT
<213> ORGANISM: Mus musculus

```
<400> SEQUENCE: 21

Gly Ala Thr Ser Leu Glu Thr
1               5

<210> SEQ ID NO 22
<211> LENGTH: 11
<212> TYPE: PRT
<213> ORGANISM: Mus musculus

<400> SEQUENCE: 22

Lys Ala Ser Asp His Ile His Asn Trp Leu Ala
1               5                   10

<210> SEQ ID NO 23
<211> LENGTH: 122
<212> TYPE: PRT
<213> ORGANISM: Mus musculus

<400> SEQUENCE: 23

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Val Asn Trp Val Lys Gln Ser His Gly Glu Asn Leu Asp Trp Ile
        35                  40                  45

Gly Leu Ile Ile Pro Tyr Asn Gly Gly Thr Ser Tyr Asn His Asn Phe
    50                  55                  60

Arg Gly Lys Ala Thr Leu Thr Val Asp Lys Ser Ser Thr Ala Tyr
65                  70                  75                  80

Met Glu Leu Leu Ser Leu Thr Ser Asp Asp Ser Ala Val Tyr Tyr Cys
                85                  90                  95

Thr Arg Gly Gly Gly Asp Phe Thr Thr Gly Tyr Thr Met Asp Tyr Trp
            100                 105                 110

Gly Gln Gly Thr Ser Val Thr Val Ser Ser
        115                 120

<210> SEQ ID NO 24
<211> LENGTH: 108
<212> TYPE: PRT
<213> ORGANISM: Mus musculus

<400> SEQUENCE: 24

Asp Ile Gln Met Thr Gln Ser Ser Ser Tyr Leu Ser Val Ser Leu Gly
1               5                   10                  15

Gly Thr Val Thr Ile Asn Cys Lys Ala Ser Asp His Ile His Asn Trp
            20                  25                  30

Leu Ala Trp Tyr Gln Gln Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Gly Gly Ser Gly Lys Asp Tyr Ser Leu Ile Ile Thr Ser Leu Gln Thr
65                  70                  75                  80

Glu Asp Val Ala Thr Tyr Tyr Cys Gln Gln Tyr Trp Ser Ile Pro Trp
                85                  90                  95

Thr Phe Gly Gly Gly Thr Lys Leu Glu Ile Lys Arg
            100                 105
```

```
<210> SEQ ID NO 25
<211> LENGTH: 330
<212> TYPE: PRT
<213> ORGANISM: Homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 107
<212> TYPE: PRT
<213> ORGANISM: Homo sapiens
```

-continued

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 27
<211> LENGTH: 330
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 330
<212> TYPE: PRT
<213> ORGANISM: Artificial
<220> FEATURE:
<223> OTHER INFORMATION: human heavy chain constant region derived from
      IgG1 mutated on L234A and L235A

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 29
<211> LENGTH: 327
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 30
<211> LENGTH: 327
<212> TYPE: PRT
<213> ORGANISM: Artificial
<220> FEATURE:
<223> OTHER INFORMATION: human heavy chain constant region derived from
      IgG4 mutated onS228P

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 31
<211> LENGTH: 972
<212> TYPE: PRT
<213> ORGANISM: Homo sapiens

```
<400> SEQUENCE: 31

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
                35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65              70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
                115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
                195                 200                 205

Pro Ala Glu Leu Val Arg Ile Arg Gly Glu Ala Ala Gln Ile Val Cys
                210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
                370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415
```

```
Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Ala Cys Met Ser Ile Met Ala Leu
    515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830
```

```
Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 32
<211> LENGTH: 972
<212> TYPE: PRT
<213> ORGANISM: Artificial
<220> FEATURE:
<223> OTHER INFORMATION: mutant CSF-1R L301S Y969F

<400> SEQUENCE: 32

```
Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220
```

```
Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
        245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Ser Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
            515                 520                 525

Leu Leu Leu Leu Leu Leu Leu Leu Leu Tyr Lys Tyr Lys Gln Lys Pro
530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640
```

-continued

```
Gly Gln His Glu Asn Ile Val Asn Leu Leu Gly Ala Cys Thr His Gly
                    645                 650                 655
Gly Pro Val Leu Val Ile Thr Glu Tyr Cys Cys Tyr Gly Asp Leu Leu
            660                 665                 670
Asn Phe Leu Arg Arg Lys Ala Glu Ala Met Leu Gly Pro Ser Leu Ser
        675                 680                 685
Pro Gly Gln Asp Pro Glu Gly Gly Val Asp Tyr Lys Asn Ile His Leu
    690                 695                 700
Glu Lys Lys Tyr Val Arg Arg Asp Ser Gly Phe Ser Ser Gln Gly Val
705                 710                 715                 720
Asp Thr Tyr Val Glu Met Arg Pro Val Ser Thr Ser Ser Asn Asp Ser
                725                 730                 735
Phe Ser Glu Gln Asp Leu Asp Lys Glu Asp Gly Arg Pro Leu Glu Leu
                740                 745                 750
Arg Asp Leu Leu His Phe Ser Ser Gln Val Ala Gln Gly Met Ala Phe
            755                 760                 765
Leu Ala Ser Lys Asn Cys Ile His Arg Asp Val Ala Ala Arg Asn Val
        770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
        835                 840                 845
Phe Ser Leu Gly Leu Asn Pro Tyr Pro Gly Ile Leu Val Asn Ser Lys
850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Ser Glu Leu Glu Glu
930                 935                 940
Glu Ser Ser Ser Glu His Leu Thr Cys Cys Glu Gln Gly Asp Ile Ala
945                 950                 955                 960
Gln Pro Leu Leu Gln Pro Asn Asn Phe Gln Phe Cys
                965                 970
```